(12) United States Patent
Anton et al.

(10) Patent No.: US 9,822,348 B2
(45) Date of Patent: Nov. 21, 2017

(54) T7 EXPRESSION SYSTEM, METHOD FOR ITS PRODUCTION AND USE THEREOF FOR PRODUCING RECOMBINANT PROTEINS

(71) Applicant: Wacker Chemie AG, Munich (DE)

(72) Inventors: Andreas Anton, Halle (DE); Monique Janowski-Egler, Halle (DE); Markus Liebscher, Halle (DE)

(73) Assignee: Wacker Chemie AG, Munich (DE)

( * ) Notice: Subject to any disclaimer, the term of this patent is extended or adjusted under 35 U.S.C. 154(b) by 0 days.

(21) Appl. No.: 15/316,232

(22) PCT Filed: Jun. 17, 2015

(86) PCT No.: PCT/EP2015/063575
§ 371 (c)(1),
(2) Date: Dec. 5, 2016

(87) PCT Pub. No.: WO2016/000961
PCT Pub. Date: Jan. 7, 2016

(65) Prior Publication Data
US 2017/0152491 A1 Jun. 1, 2017

(30) Foreign Application Priority Data
Jul. 1, 2014 (DE) .......................... 10 2014 212 675

(51) Int. Cl.
*C12N 9/12* (2006.01)
*C12N 15/72* (2006.01)
*C12N 15/70* (2006.01)

(52) U.S. Cl.
CPC ........... *C12N 9/1247* (2013.01); *C12N 15/70* (2013.01); *C12N 15/72* (2013.01); *C12Y 207/07006* (2013.01)

(58) Field of Classification Search
None
See application file for complete search history.

(56) References Cited

U.S. PATENT DOCUMENTS 5,824,528 A 10/1998 Studier et al.
2007/0015248 A1 1/2007 Anton et al.

FOREIGN PATENT DOCUMENTS

WO 2005061716 A2 7/2005

OTHER PUBLICATIONS

Datsenko et al. (2000). One-step inactivation of chromosomal genes in *Escherichia coli* K-12 using PCR products. Proceedings of the National Academy of Sciences, 97(12), 6640-6645.
De Moerlooze et al. (1992). Stabilization of T7-promoter-based pARHS expression vectors using the parB locus. Gene, 119(1), 91-93.
Dubendorff et al. (1991). Creation of a T7 autogene: Cloning and expression of the gene for bacteriophage T7 RNA polymerase under control of its cognate promoter. Journal of molecular biology, 219(1), 61-68.
Fiedler et al. (2001). proBA complementation of an auxotrophic *E coli* strain improves plasmid stability and expression yield during fermenter production of a recombinant antibody fragment. Gene, 274(1), 111-118.
Peubez et al. (2010). Antibiotic-free selection in *E coli*: new considerations for optimal design and improved production. Microbial cell factories, 9(65), 1-10.
Sengupta et al. (2011). Prevalence and significance of plasmid maintenance functions in the virulence plasmids of pathogenic bacteria. Infection and immunity, 79(7), 2502-2509.
Walia et al. (2007). Development of expression vectors for *Escherichia coli* based on the pCR2 replicon. Microbial cell factories, 6(14), 1-9.
International Search Report from PCT/EP2015/063575 dated Aug. 26, 2015.

*Primary Examiner* — Channing S Mahatan
(74) *Attorney, Agent, or Firm* — Caesar Rivise, PC

(57) ABSTRACT

The invention relates to an expression system comprising a prokaryotic cell which contains a polynucleotide construct that encodes a T7 RNA polymerase under the control of a T7 promoter and under the control of an inducible promoter. The invention also relates to an expression vector which contains a gene that encodes a protein to be expressed under the control of a T7 promoter, characterized in that said expression vector comprises a plasmid stabilization system.

7 Claims, 6 Drawing Sheets

SEQUENCE LISTING

```
<160> NUMBER OF SEQ ID NOS: 44

<210> SEQ ID NO 1
<211> LENGTH: 5990
<212> TYPE: DNA
<213> ORGANISM: Artificial Sequence
<220> FEATURE:
<223> OTHER INFORMATION: chromosomal T7 RNA polymerase construct

<400> SEQUENCE: 1
acagtcctgc taaaacgttc gtttgatatc attttcctg acaccatcga atggcgcaaa      60
acctttcgcg gtatggcatg atagcgcccg gaagagagtc aattcagggt ggtgaatgtg     120
aaaccagtaa cgttatacga tgtcgcagag tatgccggtg tctcttatca gaccgtttcc     180
cgcgtggtga accaggccag ccacgtttct gcgaaaacgc gggaaaaagt ggaagcggcg     240
atggcggagc tgaattacat tcccaaccgc gtggcacaac aactggcggg caaacagtcg     300
ttgctgattg gcgttgccac ctccagtctg gccctgcacg cgccgtcgca aattgtcgcg     360
gcgattaaat ctcgcgccga tcaactgggt gccagcgtgg tggtgtcgat ggtagaacga     420
agcggcgtcg aagcctgtaa agcggcggtg cacaatcttc tcgcgcaacg cgtcagtggg     480
ctgatcatta actatccgct ggatgaccag gatgccattg ctgtggaagc tgcctgcact     540
aatgttccgg cgttatttct tgatgtctct gaccagacac ccatcaacag tattattttc     600
tcccatgaag acggtacgcg actgggcgtg gagcatctgg tcgcattggg tcaccagcaa     660
atcgcgctgt tagcgggccc attaagttct gtctcggcgc gtctgcgtct ggctggctgg     720
```

```
cataaatatc tcactcgcaa tcaaattcag ccgatagcgg aacgggaagg cgactggagt      780
gccatgtccg gttttcaaca aaccatgcaa atgctgaatg agggcatcgt tcccactgcg      840
atgctggttg ccaacgatca gatggcgctg ggcgcaatgc gcgccattac cgagtccggg      900
ctgcgcgttg tgcggatat ctcggtagtg ggatacgacg ataccgaaga cagctcatgt      960
tatatcccgc cgttaaccac catcaaacag gattttcgcc tgctgggca aaccagcgtg     1020 gaccgcttgc tgcaactctc tcagggccag gcggtgaagg gcaatcagct gttgcccgtc     1080
tcactggtga aagaaaaac caccctggcg cccaatacgc aaaccgcctc tccccgcgcg     1140
ttggccgatt cattaatgca gctggcacga caggtttccc gactggaaag cgggcagtga     1200
gcgcaacgca attaatgtaa gttagctcac tcattaggca ccccaggctt tacactttat     1260
gcttccggct cgtataatgt gtggaattgt gagcggataa caatttcaca caggaaacag     1320
ctatgaccat gattacggat tcactggccg tcgttttaca acgtcgtgac tgggaaaacc     1380
ctggcgttac ccaacttaat cgccttgcag cacatcccc tttcgccagc tggcgtaata     1440
gcgaagaggc ccgcaccgat cgcccttccc aacagttgcg cagcctgaat ggcgaatggc     1500
gctttgcctg gttccggca ccagaagcgg tgccggaaag ctggctggag tgcgatcttc     1560
ctgaggccga tactgtcgtc gtcccctcaa actggcagat gcacggttac gatgcgccca     1620
tctacaccaa cgtgacctat cccattacgg tcaatccgcc gtttgttccc acggagaatc     1680
cgacgggttg ttactcgctc acatttaatg ttgatgaaag ctggctacag gaaggccaga     1740
cgcgaattat ttttgatggc gtcgggatct gatccggatt tactaactgg aagaggcact     1800
aaatgaacac gattaacatc gctaagaacg acttctctga catcgaactg gctgctatcc     1860
cgttcaacac tctggctgac cattacggtg agcgtttagc tcgcgaacag ttggcccttg     1920
agcatgagtc ttacgagatg ggtgaagcac gcttccgcaa gatgtttgag cgtcaactta     1980
aagctggtga ggttgcggat aacgctgccg ccaagcctct catcactacc ctactcccta     2040
agatgattgc acgcatcaac gactggtttg aggaagtgaa agctaagcgc ggcaagcgcc     2100
cgacagcctt ccagttcctg caagaaatca agcggaagc cgtagcgtac atcaccatta     2160
agaccactct ggcttgccta accagtgctg acaatacaac cgttcaggct gtagcaagcg     2220
caatcggtcg ggccattgag gacgaggctc gcttcggtcg tatccgtgac cttgaagcta     2280
agcacttcaa gaaaaacgtt gaggaacaac tcaacaagcg cgtagggcac gtctacaaga     2340
aagcatttat gcaagttgtc gaggctgaca tgctctctaa gggtctactc ggtggcgagg     2400
cgtggtcttc gtggcataag gaagactcta ttcatgtagg agtacgctgc atcgagatgc     2460
tcattgagtc aaccggaatg gttagcttac accgccaaaa tgctggcgta gtaggtcaag     2520
actctgagac tatcgaactc gcacctgaat acgctgaggc tatcgcaacc cgtgcaggtg     2580
cgctggctgg catctctccg atgttccaac cttgcgtagt tcctcctaag ccgtggactg     2640
gcattactgg tggtggctat tgggctaacg gtcgtcgtcc tctggcgctg gtgcgtactc     2700
acagtaagaa agcactgatg cgctacgaag acgtttacat gcctgaggtg tacaaagcga     2760
ttaacattgc gcaaaacacc gcatggaaaa tcaacaagaa agtcctagcg gtcgccaacg     2820
taatcaccaa gtggaagcat tgtccggtcg aggacatccc tgcgattgag cgtgaagaac     2880
tcccgatgaa accggaagac atcgacatga atcctgaggc tctcaccgcg tggaaacgtg     2940
ctgccgctgc tgtgtaccgc aaggacaagg ctcgcaagtc tcgccgtatc agccttgagt     3000
tcatgcttga gcaagccaat aagtttgcta accataaggc catctggttc ccttacaaca     3060
```

-continued

| | |
|---|---|
| tggactggcg cggtcgtgtt tacgctgtgt caatgttcaa cccgcaaggt aacgatatga | 3120 |
| ccaaaggact gcttacgctg gcgaaaggta aaccaatcgg taaggaaggt tactactggc | 3180 |
| tgaaaatcca cggtgcaaac tgtgcgggtg tcgataaggt tccgttccct gagcgcatca | 3240 |
| agttcattga ggaaaaccac gagaacatca tggcttgcgc taagtctcca ctggagaaca | 3300 |
| cttggtgggc tgagcaagat tctccgttct gcttccttgc gttctgcttt gagtacgctg | 3360 |
| gggtacagca ccacggcctg agctataact gctcccttcc gctggcgttt gacgggtctt | 3420 |
| gctctggcat ccagcacttc tccgcgatgc tccgagatga ggtaggtggt cgcgcggtta | 3480 |
| acttgcttcc tagtgaaacc gttcaggaca tctacgggat tgttgctaag aaagtcaacg | 3540 |
| agattctaca agcagacgca atcaatggga ccgataacga agtagttacc gtgaccgatg | 3600 |
| agaacactgg tgaaatctct gagaaagtca agctgggcac taaggcactg gctggtcaat | 3660 |
| ggctggctta cggtgttact cgcagtgtga ctaagcgttc agtcatgacg ctggcttacg | 3720 |
| ggtccaaaga gttcggcttc cgtcaacaag tgctggaaga taccattcag ccagctattg | 3780 |
| attccggcaa gggtctgatg ttcactcagc cgaatcaggt tgctggatac atggctaagc | 3840 |
| tgatttggga atctgtgagc gtgacggtgg tagctgcggt tgaagcaatg aactggctta | 3900 |
| agtctgctgc taagctgctg gctgctgagg tcaaagataa gaagactgga gagattcttc | 3960 |
| gcaagcgttg cgctgtgcat tgggtaactc ctgatggttt ccctgtgtgg caggaataca | 4020 |
| agaagcctat tcagacgcgc ttgaacctga tgttcctcgg tcagttccgc ttacagccta | 4080 |
| ccattaacac caacaaagat agcgagattg atgcacacaa acaggagtct ggtatcgctc | 4140 |
| ctaactttgt acacagccaa gacggtagcc accttcgtaa gactgtagtg tgggcacacg | 4200 |
| agaagtacgg aatcgaatct tttgcactga ttcacgactc cttcggtacc attccggctg | 4260 |
| acgctgcgaa cctgttcaaa gcagtgcgcg aaactatggt tgacacatat gagtcttgtg | 4320 |
| atgtactggc tgatttctac gaccagttcg ctgaccagtt gcacgagtct caattggaca | 4380 |
| aaatgccagc acttccggct aaaggtaact tgaacctccg tgacatctta gagtcggact | 4440 |
| tcgcgttcgc gtaaaagctt gcgattgtgt aggctggagc tgcttcgaag ttcctatact | 4500 |
| ttctagagaa taggaacttc ggaataggaa cttcaagatc ccctcacgct gccgcaagca | 4560 |
| ctcagggcgc aagggctgct aaaggaagcg gaacacgtag aaagccagtc cgcagaaacg | 4620 |
| gtgctgaccc cggatgaatg tcagctactg ggctatctgg acaagggaaa acgcaagcgc | 4680 |
| aaagagaaag caggtagctt gcagtgggct tacatggcga tagctagact gggcggtttt | 4740 |
| atggacagca agcgaaccgg aattgccagc tggggcgccc tctggtaagg ttgggaagcc | 4800 |
| ctgcaaagta aactggatgg ctttcttgcc gccaaggatc tgatggcgca ggggatcaag | 4860 |
| atctgatcaa gagacaggat gaggatcgtt tcgcatgatt gaacaagatg gattgcacgc | 4920 |
| aggttctccg gccgcttggg tggagaggct attcggctat gactgggcac aacagacaat | 4980 |
| cggctgctct gatgccgccg tgttccggct gtcagcgcag gggcgcccgg ttcttttgt | 5040 |
| caagaccgac ctgtccggtg ccctgaatga actgcaggac gaggcagcgc ggctatcgtg | 5100 |
| gctggccacg acgggcgttc cttgcgcagc tgtgctcgac gttgtcactg aagcgggaag | 5160 |
| ggactggctg ctattgggcg aagtgccggg gcaggatctc ctgtcatctc accttgctcc | 5220 |
| tgccgagaaa gtatccatca tggctgatgc aatgcggcgg ctgcatacgc ttgatccggc | 5280 |
| tacctgccca ttcgaccacc aagcgaaaca tcgcatcgag cgagcacgta ctcggatgga | 5340 |
| agccggtctt gtcgatcagg atgatctgga cgaagagcat caggggctcg cgccagccga | 5400 |
| actgttcgcc aggctcaagg cgcgcatgcc cgacggcgag gatctcgtcg tgacccatgg | 5460 |

```
cgatgcctgc ttgccgaata tcatggtgga aaatggccgc tttttctggat tcatcgactg    5520 tggccggctg ggtgtggcgg accgctatca ggacatagcg ttggctaccc gtgatattgc    5580
tgaagagctt ggcggcgaat gggctgaccg cttcctcgtg ctttacggta tcgccgctcc    5640
cgattcgcag cgcatcgcct tctatcgcct tcttgacgag ttcttctgag cgggactctg    5700
gggttcgaaa tgaccgacca agcgacgccc aacctgccat cacgagattt cgattccacc    5760
gccgccttct atgaaaggtt gggcttcgga atcgttttcc gggacgccgg ctggatgatc    5820
ctccagcgcg gggatctcat gctggagttc ttcgcccacc ccagcttcaa aagcgctctg    5880
aagttcctat actttctaga aataggaac ttcggaatag gaactaagga ggatattcat    5940
atggaccatg ggattcacaa ggccattgac gcatcgcccg gttagttta    5990
```

```
<210> SEQ ID NO 2
<211> LENGTH: 34
<212> TYPE: DNA
<213> ORGANISM: Artificial Sequence
<220> FEATURE:
<223> OTHER INFORMATION: Primer

<400> SEQUENCE: 2
taaaaagctt gactcctgtt gatagatcca gtaa                                34

<210> SEQ ID NO 3
<211> LENGTH: 31
<212> TYPE: DNA
<213> ORGANISM: Artificial Sequence
<220> FEATURE:
<223> OTHER INFORMATION: Primer

<400> SEQUENCE: 3
aaaacatgta ttctcaccaa taaaaaacgc c                                   31

<210> SEQ ID NO 4
<211> LENGTH: 25
<212> TYPE: DNA
<213> ORGANISM: Artificial Sequence
<220> FEATURE:
<223> OTHER INFORMATION: Primer

<400> SEQUENCE: 4
aagggcccgc cacgttgtgt gtctc                                          25

<210> SEQ ID NO 5
<211> LENGTH: 31
<212> TYPE: DNA
<213> ORGANISM: Artificial Sequence
<220> FEATURE:
<223> OTHER INFORMATION: Primer

<400> SEQUENCE: 5
aaagctagcg atatcgccgt cccgtcaagt c                                   31

<210> SEQ ID NO 6
<211> LENGTH: 28
<212> TYPE: DNA
<213> ORGANISM: Artificial Sequence
<220> FEATURE:
<223> OTHER INFORMATION: Primer

<400> SEQUENCE: 6
aaagctagcg ggaataaggg cgacacgg                                       28
```

```
<210> SEQ ID NO 7
<211> LENGTH: 30
<212> TYPE: DNA
<213> ORGANISM: Artificial Sequence
<220> FEATURE:
<223> OTHER INFORMATION: Primer

<400> SEQUENCE: 7
aaagggccca cgtgagtttt cgttccactg                                              30

<210> SEQ ID NO 8
<211> LENGTH: 39
<212> TYPE: DNA
<213> ORGANISM: Artificial Sequence
<220> FEATURE:
<223> OTHER INFORMATION: Primer

<400> SEQUENCE: 8
caatggtcag aaattggtta attggttgta acactggca                                    39

<210> SEQ ID NO 9
<211> LENGTH: 23
<212> TYPE: DNA
<213> ORGANISM: Artificial Sequence
<220> FEATURE:
<223> OTHER INFORMATION: Primer

<400> SEQUENCE: 9
gggcccacgt gagttttcgt tcc                                                     23

<210> SEQ ID NO 10
<211> LENGTH: 31
<212> TYPE: DNA
<213> ORGANISM: Artificial Sequence
<220> FEATURE:
<223> OTHER INFORMATION: Primer

<400> SEQUENCE: 10
caattggcca cgttgtgtgt ctcaaaatct c                                            31

<210> SEQ ID NO 11
<211> LENGTH: 28
<212> TYPE: DNA
<213> ORGANISM: Artificial Sequence
<220> FEATURE:
<223> OTHER INFORMATION: Primer

<400> SEQUENCE: 11
gggcccgata tcgccgtccc gtcaagtc                                                28

<210> SEQ ID NO 12
<211> LENGTH: 29
<212> TYPE: DNA
<213> ORGANISM: Artificial Sequence
<220> FEATURE:
<223> OTHER INFORMATION: Primer

<400> SEQUENCE: 12
aaagggcccg caaccgacga cagtcctgc                                               29

<210> SEQ ID NO 13
<211> LENGTH: 29
<212> TYPE: DNA
<213> ORGANISM: Artificial Sequence
<220> FEATURE:
<223> OTHER INFORMATION: Primer
```

<400> SEQUENCE: 13
aaagggcccc ggtggacaaa ggttaaaac                                         29

<210> SEQ ID NO 14
<211> LENGTH: 27
<212> TYPE: DNA
<213> ORGANISM: Artificial Sequence
<220> FEATURE:
<223> OTHER INFORMATION: Primer

<400> SEQUENCE: 14
aaagctagcg acaccatcga atggcgc                                           27

<210> SEQ ID NO 15
<211> LENGTH: 25
<212> TYPE: DNA
<213> ORGANISM: Artificial Sequence
<220> FEATURE:
<223> OTHER INFORMATION: Primer

<400> SEQUENCE: 15
aaagctagct cactgcccgc tttcc                                             25

<210> SEQ ID NO 16
<211> LENGTH: 33
<212> TYPE: DNA
<213> ORGANISM: Artificial Sequence
<220> FEATURE:
<223> OTHER INFORMATION: Primer

<400> SEQUENCE: 16
aaacaattgg aaattaatac gactcactat agg                                    33

<210> SEQ ID NO 17
<211> LENGTH: 40
<212> TYPE: DNA
<213> ORGANISM: Artificial Sequence
<220> FEATURE:
<223> OTHER INFORMATION: Primer

<400> SEQUENCE: 17
aaagaattct ctccttctta agttaaaca aaattatttc                              40

<210> SEQ ID NO 18
<211> LENGTH: 27
<212> TYPE: DNA
<213> ORGANISM: Artificial Sequence
<220> FEATURE:
<223> OTHER INFORMATION: Primer

<400> SEQUENCE: 18
acggctacac tagaaggaca gtatttg                                           27

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19
agttaggcca ccacttcaag                                                   20

<210> SEQ ID NO 20

<211> LENGTH: 6357
<212> TYPE: DNA
<213> ORGANISM: Artificial Sequence
<220> FEATURE:
<223> OTHER INFORMATION: Expression vector

<400> SEQUENCE: 20

| | |
|---|---|
| gaattggaaa ttaatacgac tcactatagg ggaattgtga gcggataaca attcccctct | 60 |
| agaaataatt ttgtttaact ttaagaagga gagaattcga gctcggtacc cggggatcct | 120 |
| ctagagtcga cctgcaggca tgcaagcttg actcctgttg atagatccag taatgacctc | 180 |
| agaactccat ctggatttgt tcagaacgct cggttgccgc cgggcgtttt ttattggtga | 240 |
| gaatacatgt gagcaaaagg ccagcaaaag gccaggaacc gtaaaaaggc cgcgttgctg | 300 |
| gcgttttttcc ataggctccg ccccccctgac gagcatcaca aaaatcgacg ctcaagtcag | 360 |
| aggtggcgaa acccgacagg actataaaga taccaggcgt ttccccctgg aagctccctc | 420 |
| gtgcgctctc ctgttccgac cctgccgctt accggatacc tgtccgcctt tctcccttcg | 480 |
| ggaagcgtgg cgctttctca tagctcacgc tgtaggtatc tcagttcggt gtaggtcgtt | 540 |
| cgctccaagc tgggctgtgt gcacgaaccc ccgttcagc ccgaccgctg cgccttatcc | 600 |
| ggtaactatc gtcttgagtc aacccggta agacacgact tatcgccact ggcagcagcc | 660 |
| actggtaaca ggattagcag agcgaggtat gtaggcggtg ctacagagtt cttgaagtgg | 720 |
| tggcctaact acggctacac tagaaggaca gtatttggta tctgcgctct gctgaagcca | 780 |
| gttaccttcg gaaaaagagt tggtagctct tgatccggca acaaaccac cgctggtagc | 840 |
| ggtggttttt tgtttgcaa gcagcagatt acgcgcagaa aaaaggatc tcaagaagat | 900 |
| cctttgatct tttctacggg gtctgacgct cagtggaacg aaaactcacg tgggccgggc | 960 |
| ccgcaaccga cgacagtcct gctaaaacgt tcgtttgata tcattttcc taaaattgaa | 1020 |
| tggcagagaa tcatgagtga cagccagacg ctggtggtaa aactcggcac cagtgtgcta | 1080 |
| acaggcggat cgcgccgtct gaaccgtgcc catatcgttg aacttgttcg ccagtgcgcg | 1140 |
| cagttacatg ccgccgggca tcggattgtt attgtgacgt cgggcgcgat cgccgccgga | 1200 |
| cgtgagcacc tgggttaccc ggaactgcca gcgaccatcg cctcgaaaca actgctggcg | 1260 |
| gcggtagggc agagtcgact gattcaactg tgggaacagc tgttttcgat ttatggcatt | 1320 |
| cacgtcgggg aaatgctgct gaccgtgct gatatggaag accgtgaacg cttcctgaac | 1380 |
| gcccgcgaca ccctgcgagc gttgctcgat aacaatatcg ttccggtaat caatgagaac | 1440 |
| gatgctgtcg ctacggcaga gattaaggtc ggcgataacg ataacctttc tgcgctggcg | 1500 |
| gcgattcttg cgggtgccga taactgttg ctgctgaccg atcaaaaagg tttgtatacc | 1560 |
| gctgacccgc gcagcaatcc gcaggcagaa ctgattaaag atgtttacgg cattgatgac | 1620 |
| gcactgcgcg cgattgccgg tgacagcgtt tcaggcctcg gaactggcgg catgagtacc | 1680 |
| aaattgcagg ccgctgacgt ggcttgccgt gcgggtatcg acaccattat tgccgcgggc | 1740 |
| agcaagccgg gcgttattgg tgatgtgatg gaaggcattt ccgtcggtac gctgttccat | 1800 |
| gcccaggcga ctccgcttga aaaccgtaaa cgctggattt tcggtgcgcc gccggcgggt | 1860 |
| gaaatcacgg tagatgaagg ggcaactgcc gccattctgg aacgcggcag ctccctgttg | 1920 |
| ccgaaaggca ttaaaagcgt gactggcaat ttctcgcgtg gtgaagtcat ccgcatttgc | 1980 |
| aacctcgaag gccgcgatat cgcccacggc gtcagtcgtt acaacagcga tgcattacgc | 2040 |
| cgtattgccg gacaccactc gcaagaaatt gatgcaatac tggatatga atacggcccg | 2100 |
| gttgccgttc accgtgatga catgattacc cgttaaggag caggctgatg ctggaacaaa | 2160 |

```
tgggcattgc cgcgaagcaa gcctcgtata aattagcgca actctccagc cgcgaaaaaa   2220
atcgcgtgct ggaaaaaatc gccgatgaac tggaagcaca aagcgaaatc atcctcaacg   2280
ctaacgccca ggatgttgct gacgcgcgag ccaatggcct tagcgaagcg atgcttgacc   2340
gtctggcact gacgcccgca cggctgaaag gcattgccga cgatgtacgt caggtgtgca   2400
acctcgccga tccggtgggg caggtaatcg atggcggcgt actggacagc ggcctgcgtc   2460
ttgagcgtcg tcgcgtaccg ctgggggtta ttggcgtgat ttatgaagcg cgcccgaacg   2520
tgacggttga tgtcgcttcg ctgtgcctga aaaccggtaa tgcggtgatc ctgcgcggtg   2580
gcaaagaaac gtgtcgcact aacgctgcaa cggtggcggt gattcaggac gccctgaaat   2640
cctgcggctt accggcgggt gccgtgcagg cgattgataa tcctgaccgt gcgctggtca   2700
gtgaaatgct gcgtatggat aaatacatcg acatgctgat cccgcgtggt ggcgctggtt   2760
tgcataaact gtgccgtgaa cagtcgacaa tcccggtgat cacaggtggt ataggcgtat   2820
gccatattta cgttgatgaa agtgtagaga tcgctgaagc attaaaagtg atcgtcaacg   2880
cgaaaactca gcgtccgagc acatgtaata cggttgaaac gttgctggtg aataaaaaca   2940
tcgccgatag cttcctgccc gcattaagca aacaaatggc ggaaagcggc gtgacattac   3000
acgcagatgc agctgcactg gcgcagttgc aggcaggccc tgcgaaggtg gttgctgtta   3060
aagccgaaga gtatgacgat gagtttctgt cattagattt gaacgtcaaa atcgtcagcg   3120
atcttgacga tgccatcgcc catattcgtg aacacggcac acaacactcc gatgcgatcc   3180
tgacccgcga tatgcgcaac gcccagcgtt ttgttaacga agtggattcg tccgctgttt   3240
acgttaacgc ctctacgcgt tttaccgacg gcggccagtt tggtctgggt gcggaagtgg   3300
cggtaagcac acaaaaactc cacgcgcgtg gcccaatggg gctggaagca ctgaccactt   3360
acaagtggat cggcattggt gattacacca ttcgtgcgta aataaaaccg ggtgatgcaa   3420
aagtagccat ttgattcaca aggccattga cgcatcgccc ggttagtttt aaccttgtcc   3480
accggggccc gatatcgccg tcccgtcaag tcagcgtaat gctctgccag tgttacaacc   3540
aattaaccaa ttctgattag aaaaactcat cgagcatcaa atgaaactgc aatttattca   3600
tatcaggatt atcaatacca tatttttgaa aaagccgttt ctgtaatgaa ggagaaaact   3660
caccgaggca gttccatagg atggcaagat cctggtatcg gtctgcgatt ccgactcgtc   3720
caacatcaat acaacctatt aatttcccct cgtcaaaaat aaggttatca agtgagaaat   3780
caccatgagt gacgactgaa tccggtgaga atggcaaaag cttatgcatt tctttccaga   3840
cttgttcaac aggccagcca ttacgctcgt catcaaaatc actcgcatca accaaaccgt   3900
tattcattcg tgattgcgcc tgagcgagac gaaatacgcg atcgctgtta aaaggacaat   3960
tacaaacagg aatcgaatgc aaccggcgca ggaacactgc cagcgcatca acaatatttt   4020
cacctgaatc aggatattct tctaataccg ggaatgctgt tttcccgggg atcgcagtgg   4080
tgagtaacca tgcatcatca ggagtacgga taaaatgctt gatggtcgga agaggcataa   4140
attccgtcag ccagtttagt ctgaccatct catctgtaac atcattggca acgctacctt   4200
tgccatgttt cagaaacaac tctggcgcat cgggcttccc atacaatcga tagattgtcg   4260
cacctgattg cccgacatta tcgcgagccc atttataccc atataaatca gcatccatgt   4320
tggaatttaa tcgcggcctc gagcaagacg tttcccgttg aatatggctc ataacacccc   4380
ttgtattact gtttatgtaa gcagacagtt ttattgttca tgatgatata ttttatctt   4440
gtgcaatgta acatcagaga ttttgagaca cacaacgtgg ccaattgtca gaattggtta   4500
```

```
attggttgta acactggcag agcattacgc tgacttgacg ggacggcgat atcgctagcg    4560
acaccatcga atggcgcaaa acctttcgcg gtatggcatg atagcgcccg gaagagagtc    4620
aattcagggt ggtgaatgtg aaaccagtaa cgttatacga tgtcgcagag tatgccggtg    4680
tctcttatca gaccgtttcc cgcgtggtga accaggccag ccacgtttct gcgaaaacgc    4740
gggaaaaagt ggaagcggcg atggcggagc tgaattacat tcccaaccgc gtggcacaac    4800
aactggcggg caaacagtcg ttgctgattg cgttgccac ctccagtctg gccctgcacg     4860
cgccgtcgca aattgtcgcg gcgattaaat ctcgcgccga tcaactgggt gccagcgtgg    4920
tggtgtcgat ggtagaacga agcggcgtcg aagcctgtaa agcggcggtg cacaatcttc    4980
tcgcgcaacg cgtcagtggg ctgatcatta actatccgct ggatgaccag gatgccattg    5040
ctgtggaagc tgcctgcact aatgttccgg cgttatttct tgatgtctct gaccagacac    5100
ccatcaacag tattattttc tcccatgaag acggtacgcg actgggcgtg gagcatctgg    5160
tcgcattggg tcaccagcaa atcgcgctgt tagcgggccc attaagttct gtctcggcgc    5220
gtctgcgtct ggctggctgg cataaatatc tcactcgcaa tcaaattcag ccgatagcgg    5280
aacgggaagg cgactggagt gccatgtccg gttttcaaca aaccatgcaa atgctgaatg    5340
agggcatcgt tcccactgcg atgctggttg ccaacgatca gatggcgctg ggcgcaatgc    5400
gcgccattac cgagtccggg ctgcgcgttg gtgcggatat ctcggtagtg ggatacgacg    5460
ataccgaaga cagctcatgt tatatcccgc cgttaaccac catcaaacag gattttcgcc    5520
tgctggggca aaccagcgtg gaccgcttgc tgcaactctc tcagggccag gcggtgaagg    5580
gcaatcagct gttgcccgtc tcactggtga aagaaaaac cacccctggcg cccaatacgc    5640
aaaccgcctc tccccgcgcg ttggccgatt cattaatgca gctggcacga caggtttccc    5700
gactggaaag cgggcagtga gctagcggga ataagggcga cacggaaatg ttgaatactc    5760
atactcttcc tttttcaata ttattgaagc atttatcagg gttattgtct catgagcgga    5820
tacatatttg aatgtattta gaaaaataaa caaatagggg ttccgcgcac atttccccga    5880
aaagtgccac ctgacgtcta agaaaccatt attatcatga cattaaccta taaaaatagg    5940
cgtatcacga ggccctttcg tctcgcgcgt ttcggtgatg acggtgaaaa cctctgacac    6000
atgcagctcc cggagacggt cacagcttgt ctgtaagcgg atgccgggag cagacaagcc    6060
cgtcagggcg cgtcagcggg tgttggcggg tgtcggggct ggcttaacta tgcggcatca    6120
gagcagattg tactgagagt gcaccatatg cggtgtgaaa taccgcacag atgcgtaagg    6180
agaaaatacc gcatcaggcg ccattcgcca ttcaggctgc gcaactgttg ggaagggcga    6240
tcggtgcggg cctcttcgct attacgccag ctggcgaaag ggggatgtgc tgcaaggcga    6300
ttaagttggg taacgccagg gttttcccag tcacgacgtt gtaaaacgac ggccagt      6357
```

<210> SEQ ID NO 21
<211> LENGTH: 32
<212> TYPE: DNA
<213> ORGANISM: Artificial Sequence
<220> FEATURE:
<223> OTHER INFORMATION: Primer

<400> SEQUENCE: 21
aaacatatgg tgaaaccatg aaaaatggca gc                                   32

<210> SEQ ID NO 22
<211> LENGTH: 28
<212> TYPE: DNA
<213> ORGANISM: Artificial Sequence

```
<220> FEATURE:
<223> OTHER INFORMATION: Primer

<400> SEQUENCE: 22
aaacatatgc tcgatggcta cgagggca                                              28

<210> SEQ ID NO 23
<211> LENGTH: 6604
<212> TYPE: DNA
<213> ORGANISM: Artificial Sequence
<220> FEATURE:
<223> OTHER INFORMATION: Expression vector

<400> SEQUENCE: 23
gaattggaaa ttaatacgac tcactatagg ggaattgtga gcggataaca attcccctct    60
agaaataatt ttgtttaact ttaagaagga gagaattcga gctcggtacc cggggatcct   120
ctagagtcga cctgcaggca tgcaagcttg actcctgttg atagatccag taatgacctc   180
agaactccat ctggatttgt tcagaacgct cggttgccgc cgggcgtttt ttattggtga   240
gaatacatgt gagcaaaagg ccagcaaaag gccaggaacc gtaaaaaggc cgcgttgctg   300
gcgtttttcc ataggctccg ccccctgac gagcatcaca aaaatcgacg ctcaagtcag   360
aggtggcgaa acccgacagg actataaaga taccaggcgt ttccccctgg aagctccctc   420
gtgcgctctc ctgttccgac cctgccgctt accggatacc tgtccgcctt ctcccttcg    480 ggaagcgtgg cgctttctca tagctcacgc tgtaggtatc tcagttcggt gtaggtcgtt   540
cgctccaagc tgggctgtgt gcacgaaccc cccgttcagc ccgaccgctg cgccttatcc   600
ggtaactatc gtcttgagtc aacccggta agacacgact tatcgccact ggcagcagcc   660
actggtaaca ggattagcag agcgaggtat gtaggcggtg ctacagagtt cttgaagtgg   720
tggcctaact acggctacac tagaaggaca gtatttggta tctgcgctct gctgaagcca   780
gttaccttcg gaaaaagagt tggtagctct tgatccggca acaaaccac cgctggtagc   840 ggtggttttt ttgtttgcaa gcagcagatt acgcgcagaa aaaaggatc tcaagaagat   900 cctttgatct tttctacggg gtctgacgct cagtggaacg aaaactcacg tgggccgggc   960
ccgcaaccga cgacagtcct gctaaaacgt tcgtttgata tcatttttcc taaaattgaa  1020
tggcagagaa tcatgagtga cagccagacg ctggtggtaa aactcggcac cagtgtgcta  1080
acaggcggat cgcgccgtct gaaccgtgcc catatcgttg aacttgttcg ccagtgcgcg  1140
cagttacatg ccgccgggca tcggattgtt attgtgacgt cgggcgcgat cgccgccgga  1200
cgtgagcacc tgggttaccc ggaactgcca gcgaccatcg cctcgaaaca actgctggcg  1260
gcggtagggc agagtcgact gattcaactg tgggaacagc tgttttcgat ttatggcatt  1320
cacgtcgggc aaatgctgct gacccgtgct gatatgaag accgtgaacg cttcctgaac  1380
gcccgcgaca ccctgcgagc gttgctcgat aacaatatcg ttccggtaat caatgagaac  1440
gatgctgtcg ctacggcaga gattaaggtc ggcgataaca taaccttctg cgctggcg    1500 gcgattcttg cgggtgccga taaactgttg ctgctgaccg atcaaaaagg tttgtatacc  1560
gctgacccgc gcagcaatcc gcaggcagaa ctgattaaag atgtttacgg cattgatgac  1620
gcactgcgcg cgattccgg tgacagcgtt tcaggcctcg gaactggcgg catgagtacc  1680
aaattgcagg ccgctgacgt ggcttgccgt gcgggtatcg acaccattat tgccgcgggc  1740
agcaagccgg gcgttattgg tgatgtgatg gaaggcattt ccgtcggtac gctgttccat  1800
gcccaggcga ctccgcttga aaaccgtaaa cgctggattt cggtgcgcc gccggcgggt  1860
```

```
gaaatcacgg tagatgaagg ggcaactgcc gccattctgg aacgcggcag ctccctgttg     1920
ccgaaaggca ttaaaagcgt gactggcaat ttctcgcgtg gtgaagtcat ccgcatttgc     1980
aacctcgaag gccgcgatat cgcccacggc gtcagtcgtt acaacagcga tgcattacgc     2040
cgtattgccg acaccactc gcaagaaatt gatgcaatac tgggatatga atacggcccg      2100
gttgccgttc accgtgatga catgattacc cgttaaggag caggctgatg ctggaacaaa     2160
tgggcattgc cgcgaagcaa gcctcgtata aattagcgca actctccagc cgcgaaaaaa     2220
atcgcgtgct ggaaaaaatc gccgatgaac tggaagcaca aagcgaaatc atcctcaacg     2280
ctaacgccca ggatgttgct gacgcgcgag ccaatggcct tagcgaagcg atgcttgacc     2340
gtctggcact gacgcccgca cggctgaaag gcattgccga cgatgtacgt caggtgtgca     2400
acctcgccga tccggtgggg caggtaatcg atggcgcgt actggacagc ggcctgcgtc      2460
ttgagcgtcg tcgcgtaccg ctgggggtta ttggcgtgat ttatgaagcg cgcccgaacg     2520
tgacggttga tgtcgcttcg ctgtgcctga aaaccggtaa tgcggtgatc ctgcgcggtg     2580
gcaaagaaac gtgtcgcact aacgctgcaa cggtggcggt gattcaggac gccctgaaat     2640
cctgcggctt accggcgggt gccgtgcagg cgattgataa tcctgaccgt gcgctggtca     2700
gtgaaatgct gcgtatggat aaatacatcg acatgctgat cccgcgtggt ggcgctggtt     2760
tgcataaact gtgccgtgaa cagtcgacaa tcccggtgat cacaggtggt ataggcgtat     2820
gccatattta cgttgatgaa agtgtagaga tcgctgaagc attaaaagtg atcgtcaacg     2880
cgaaaactca gcgtccgagc acatgtaata cggttgaaac gttgctggtg aataaaaaca     2940
tcgccgatag cttcctgccc gcattaagca aacaaatggc ggaaagcggc gtgacattac     3000
acgcagatgc agctgcactg gcgcagttgc aggcaggccc tgcgaaggtg gttgctgtta     3060
aagccgaaga gtatgacgat gagtttctgt cattagattt gaacgtcaaa atcgtcagcg     3120
atcttgacga tgccatcgcc catattcgtg aacacggcac acaacactcc gatgcgatcc     3180
tgacccgcga tatgcgcaac gcccagcgtt ttgttaacga agtggattcg tccgctgttt     3240
acgttaacgc ctctacgcgt tttaccgacg gcggccagtt tggtctgggt gcggaagtgg     3300
cggtaagcac acaaaaactc cacgcgcgtg gcccaatggg gctggaagca ctgaccactt     3360
acaagtggat cggcattggt gattacacca ttcgtgcgta aataaaaccg ggtgatgcaa     3420
aagtagccat ttgattcaca aggccattga cgcatcgccc ggttagtttt aaccttgtcc     3480
accggggccc gatatcgccg tcccgtcaag tcagcgtaat gctctgccag tgttacaacc     3540
aattaaccaa ttctgattag aaaaactcat cgagcatcaa atgaaactgc aatttattca     3600
tatcaggatt atcaatacca tattttttgaa aaagccgttt ctgtaatgaa ggagaaaact     3660
caccgaggca gttccatagg atggcaagat cctggtatcg gtctgcgatt ccgactcgtc     3720
caacatcaat acaacctatt aatttcccct cgtcaaaaat aaggttatca agtgagaaat     3780
caccatgagt gacgactgaa tccggtgaga atggcaaaag cttatgcatt tctttccaga     3840
cttgttcaac aggccagcca ttacgctcgt catcaaaatc actcgcatca accaaaccgt     3900
tattcattcg tgattgcgcc tgagcgagac gaaatacgcg atcgctgtta aaaggacaat     3960
tacaaacagg aatcgaatgc aaccggcgca ggaacactgc cagcgcatca acaatatttt     4020
cacctgaatc aggatattct tctaatacct ggaatgctgt tttcccgggg atcgcagtgg     4080
tgagtaacca tgcatcatca ggagtacgga taaaatgctt gatggtcgga agaggcataa     4140
attccgtcag ccagtttagt ctgaccatct catctgtaac atcattggca acgctacctt     4200
tgccatgttt cagaaacaac tctggcgcat cgggcttccc atacaatcga tagattgtcg     4260
```

```
cacctgattg cccgacatta tcgcgagccc atttataccc atataaatca gcatccatgt    4320
tggaatttaa tcgcggcctc gagcaagacg tttcccgttg aatatggctc ataacacccc    4380
ttgtattact gtttatgtaa gcagacagtt ttattgttca tgatgatata tttttatctt    4440
gtgcaatgta acatcagaga ttttgagaca cacaacgtgg ccaattgtca gaattggtta    4500
attggttgta acactggcag agcattacgc tgacttgacg ggacggcgat atcgctagcg    4560
acaccatcga atggcgcaaa acctttcgcg gtatggcatg atagcgcccg gaagagagtc    4620
aattcagggt ggtgaatgtg aaaccagtaa cgttatacga tgtcgcagag tatgccggtg    4680
tctcttatca gaccgtttcc cgcgtggtga accaggccag ccacgtttct gcgaaaacgc    4740
gggaaaaagt ggaagcggcg atggcggagc tgaattacat tcccaaccgc gtggcacaac    4800
aactggcggg caaacagtcg ttgctgattg gcgttgccac ctccagtctg gccctgcacg    4860
cgccgtcgca aattgtcgcg gcgattaaat ctcgcgccga tcaactgggt gccagcgtgg    4920
tggtgtcgat ggtagaacga agcggcgtcg aagcctgtaa agcggcggtg cacaatcttc    4980
tcgcgcaacg cgtcagtggg ctgatcatta actatccgct ggatgaccag gatgccattg    5040
ctgtggaagc tgcctgcact aatgttccgg cgttatttct tgatgtctct gaccagacac    5100
ccatcaacag tattatttc tcccatgaag acggtacgcg actgggcgtg gagcatctgg     5160
tcgcattggg tcaccagcaa atcgcgctgt tagcgggccc attaagttct gtctcggcgc    5220
gtctgcgtct ggctggctgg cataaatatc tcactcgcaa tcaaattcag ccgatagcgg    5280
aacgggaagg cgactggagt gccatgtccg gttttcaaca aaccatgcaa atgctgaatg    5340
agggcatcgt tcccactgcg atgctggttg ccaacgatca gatggcgctg ggcgcaatgc    5400
gcgccattac cgagtccggg ctgcgcgttg gtgcggatat ctcggtagtg ggatacgacg    5460
ataccgaaga cagctcatgt tatatcccgc cgttaaccac catcaaacag gattttcgcc    5520
tgctggggca aaccagcgtg gaccgcttgc tgcaactctc tcaggccag gcggtgaagg     5580 gcaatcagct gttgcccgtc tcactggtga aagaaaaac caccctggcg cccaatacgc      5640
aaaccgcctc tccccgcgcg ttggccgatt cattaatgca gctggcacga caggtttccc    5700
gactggaaag cgggcagtga gctagcggga ataagggcga cacggaaatg ttgaatactc    5760
atactcttcc ttttcaata ttattgaagc atttatcagg gttattgtct catgagcgga     5820
tacatatttg aatgtattta gaaaaataaa caaataggg ttccgcgcac atttccccga     5880
aaagtgccac ctgacgtcta agaaaccatt attatcatga cattaaccta taaaaatagg    5940
cgtatcacga ggccctttcg tctcgcgcgt ttcggtgatg acggtgaaaa cctctgacac    6000
atgcagctcc cggagacggt cacagcttgt ctgtaagcgg atgccgggag cagacaagcc    6060
cgtcagggcg cgtcagcggg tgttggcggg tgtcggggct ggcttaacta tgcggcatca    6120
gagcagattg tactgagagt gcaccatatg ctcgatggct acgagggcag acagtaagtg    6180
gatttaccat aatcccttaa ttgtacgcac cgctaaaacg cgttcagcgc gatcacggca    6240
gcagacaggt aaaaatggca acaaaccacc cgaaaaactg ccgcgatcgc gcctgataaa    6300
ttttaaccgt atgaatacct atgcaaccag agggtacagg ccacattacc cccacttaat    6360
ccactgaagc tgccattttt catggtttca ccatatgcgg tgtgaaatac cgcacagatg    6420
cgtaaggaga aaataccgca tcaggcgcca ttcgccattc aggctgcgca actgttggga    6480
agggcgatcg gtgcgggcct cttcgctatt acgccagctg gcgaaagggg gatgtgctgc    6540
aaggcgatta agttgggtaa cgccagggtt ttcccagtca cgacgttgta aaacgacggc    6600
```

```
cagt                                                              6604

<210> SEQ ID NO 24
<211> LENGTH: 30
<212> TYPE: DNA
<213> ORGANISM: Artificial Sequence
<220> FEATURE:
<223> OTHER INFORMATION: Primer

<400> SEQUENCE: 24
aaaccatggg atatcgctag cgacaccatc                                    30

<210> SEQ ID NO 25
<211> LENGTH: 30
<212> TYPE: DNA
<213> ORGANISM: Artificial Sequence
<220> FEATURE:
<223> OTHER INFORMATION: Primer

<400> SEQUENCE: 25
actagtcggt ggacaaggtt aaaactaacc                                    30

<210> SEQ ID NO 26
<211> LENGTH: 34
<212> TYPE: DNA
<213> ORGANISM: Artificial Sequence
<220> FEATURE:
<223> OTHER INFORMATION: Primer

<400> SEQUENCE: 26
aaaccatggt ctcatgtttg acagcttatc atcg                               34

<210> SEQ ID NO 27
<211> LENGTH: 29
<212> TYPE: DNA
<213> ORGANISM: Artificial Sequence
<220> FEATURE:
<223> OTHER INFORMATION: Primer

<400> SEQUENCE: 27
aaaactagtc tgtcagacca agtttactc                                     29

<210> SEQ ID NO 28
<211> LENGTH: 27
<212> TYPE: DNA
<213> ORGANISM: Artificial Sequence
<220> FEATURE:
<223> OTHER INFORMATION: Primer

<400> SEQUENCE: 28
ccatgggata tcgctagcga caccatc                                       27

<210> SEQ ID NO 29
<211> LENGTH: 25
<212> TYPE: DNA
<213> ORGANISM: Artificial Sequence
<220> FEATURE:
<223> OTHER INFORMATION: Primer

<400> SEQUENCE: 29
tctcatgttt gacagcttat catcg                                         25

<210> SEQ ID NO 30
<211> LENGTH: 6920
<212> TYPE: DNA
<213> ORGANISM: Artificial Sequence
```

<220> FEATURE:
<223> OTHER INFORMATION: Expression vector

<400> SEQUENCE: 30

```
gaattggaaa ttaatacgac tcactatagg ggaattgtga gcggataaca attcccctct    60
agaaataatt ttgtttaact ttaagaagga gagaattcga gctcggtacc cggggatcct   120
ctagagtcga cctgcaggca tgcaagcttg actcctgttg atagatccag taatgacctc   180
agaactccat ctggatttgt tcagaacgct cggttgccgc cgggcgtttt ttattggtga   240
gaatacatgt gagcaaaagg ccagcaaaag gccaggaacc gtaaaaaggc cgcgttgctg   300
gcgtttttcc ataggctccg ccccctgac gagcatcaca aaaatcgacg ctcaagtcag    360
aggtggcgaa acccgacagg actataaaga taccaggcgt ttccccctgg aagctccctc   420
gtgcgctctc ctgttccgac cctgccgctt accggatacc tgtccgcctt tctcccttcg   480
ggaagcgtgg cgctttctca tagctcacgc tgtaggtatc tcagttcggt gtaggtcgtt   540
cgctccaagc tgggctgtgt gcacgaaccc cccgttcagc ccgaccgctg cgccttatcc   600
ggtaactatc gtcttgagtc aacccggta agacacgact tatcgccact ggcagcagcc    660
actggtaaca ggattagcag agcgaggtat gtaggcggtg ctacagagtt cttgaagtgg   720
tggcctaact acggctacac tagaaggaca gtatttggta tctgcgctct gctgaagcca   780
gttaccttcg gaaaaagagt tggtagctct tgatccggca acaaaccac cgctggtagc    840
ggtggttttt ttgtttgcaa gcagcagatt acgcgcagaa aaaaggatc tcaagaagat    900
cctttgatct tttctacggg gtctgacgct cagtggaacg aaaactcacg tgggccgggc   960
ccgcaaccga cgacagtcct gctaaaacgt tcgtttgata tcattttcc taaaattgaa   1020
tggcagagaa tcatgagtga cagccagacg ctggtggtaa aactcggcac cagtgtgcta  1080
acaggcggat cgcgccgtct gaaccgtgcc catatcgttg aacttgttcg ccagtgcgcg  1140
cagttacatg ccgccgggca tcggattgtt attgtgacgt cgggcgcgat cgccgccgga  1200
cgtgagcacc tgggttaccc ggaactgcca gcgaccatcg cctcgaaaca actgctggcg  1260
gcggtagggc agagtcgact gattcaactg tgggaacagc tgttttcgat ttatggcatt  1320
cacgtcgggc aaatgctgct gacccgtgct gatatggaag accgtgaacg cttcctgaac  1380
gcccgcgaca ccctgcgagc gttgctcgat aacaatatcg ttccggtaat caatgagaac  1440
gatgctgtcg ctacggcaga gattaaggtc ggcgataacg ataaccttc tgcgctggcg   1500
gcgattcttg cgggtgccga taaactgttg ctgctgaccg atcaaaaagg tttgtatacc  1560
gctgacccgc gcagcaatcc gcaggcagaa ctgattaaaa tgtttacgg cattgatgac   1620
gcactgcgcg cgattgccgg tgacagcgtt tcaggcctcg aactggcgg catgagtacc   1680
aaattgcagg ccgctgacgt ggcttgccgt gcgggtatcg acaccattat tgccgcgggc  1740
agcaagccgg gcgttattgg tgatgtgatg aaggcattt ccgtcggtac gctgttccat   1800
gcccaggcga ctccgcttga aaaccgtaaa cgctggattt cggtgcgcc gccggcgggt   1860
gaaatcacgg tagatgaagg ggcaactgcc gccattctgg aacgcggcag ctccctgttg  1920
ccgaaaggca ttaaaagcgt gactggcaat ttctcgcgtg gtgaagtcat ccgcatttgc  1980
aacctcgaag ccgcgatat cgcccacggc gtcagtcgtt acaacagcga tgcattacgc   2040
cgtattgccg acaccactc gcaagaaatt gatgcaatac tgggatatga atacggcccg  2100
gttgccgttc accgtgatga catgattacc cgttaaggag caggctgatg ctggaacaaa  2160
tgggcattgc cgcgaagcaa gcctcgtata aattagcgca actctccagc cgcgaaaaaa  2220
```

-continued

```
atcgcgtgct ggaaaaaatc gccgatgaac tggaagcaca aagcgaaatc atcctcaacg      2280
ctaacgccca ggatgttgct gacgcgcgag ccaatggcct tagcgaagcg atgcttgacc      2340
gtctggcact gacgcccgca cggctgaaag gcattgccga cgatgtacgt caggtgtgca      2400
acctcgccga tccggtgggg caggtaatcg atggcgcgt actggacagc ggcctgcgtc       2460
ttgagcgtcg tcgcgtaccg ctgggggtta ttggcgtgat ttatgaagcg cgcccgaacg      2520
tgacggttga tgtcgcttcg ctgtgcctga aaccggtaa tgcggtgatc ctgcgcggtg       2580
gcaaagaaac gtgtcgcact aacgctgcaa cggtggcggt gattcaggac gccctgaaat     2640
cctgcggctt accggcgggt gccgtgcagg cgattgataa tcctgaccgt gcgctggtca     2700
gtgaaatgct gcgtatggat aaatacatcg acatgctgat cccgcgtggt ggcgctggtt    2760
tgcataaact gtgccgtgaa cagtcgacaa tcccggtgat cacaggtggt ataggcgtat    2820
gccatattta cgttgatgaa agtgtagaga tcgctgaagc attaaaagtg atcgtcaacg    2880
cgaaaactca gcgtccgagc acatgtaata cggttgaaac gttgctggtg aataaaaaca    2940
tcgccgatag cttcctgccc gcattaagca aacaaatggc ggaaagcggc gtgacattac    3000
acgcagatgc agctgcactg gcgcagttgc aggcaggccc tgcgaaggtg gttgctgtta    3060
aagccgaaga gtatgacgat gagtttctgt cattagattt gaacgtcaaa atcgtcagcg    3120
atcttgacga tgccatcgcc catattcgtg aacacggcac acaacactcc gatgcgatcc    3180
tgacccgcga tatgcgcaac gcccagcgtt ttgttaacga agtggattcg tccgctgttt    3240
acgttaacgc ctctacgcgt tttaccgacg gcggccagtt tggtctgggt gcggaagtgg    3300
cggtaagcac acaaaaactc cacgcgcgtg gcccaatggg gctggaagca ctgaccactt    3360
acaagtggat cggcattggt gattacacca ttcgtgcgta aataaaaccg ggtgatgcaa    3420
aagtagccat ttgattcaca aggccattga cgcatcgccc ggttagtttt aaccttgtcc    3480
accgactagt gttggtttgc gcattcacag ttctccgcaa gaattgattg gctccaattc    3540
ttggagtggt gaatccgtta gcgaggtgcc gccggcttcc attcaggtcg aggtggcccg    3600
gctccatgca ccgcgacgca acgcggggag gcagacaagg tatagggcgg cgcctacaat    3660
ccatgccaac ccgttccatg tgctcgccga ggcggcataa atcgccgtga cgatcagcgg    3720
tccaatgatc gaagttaggc tggtaagagc cgcgagcgat ccttgaagct gtccctgatg    3780
gtcgtcatct acctgcctgg acagcatggc ctgcaacgcg gcatcccga tgccgccgga     3840 agcgagaaga atcataatgg ggaaggccat ccagcctcgc gtcgcgaacg ccagcaagac    3900
gtagcccagc gcgtcggccg ccatgccggc gataatggcc tgcttctcgc cgaaacgttt    3960
ggtggcggga ccagtgacga aggcttgagc gagggcgtgc aagattccga ataccgcaag    4020
cgacaggccg atcatcgtcg cgctccagcg aaagcggtcc tcgccgaaaa tgacccagag    4080
cgctgccggc acctgtccta cgagttgcat gataaagaag acagtcataa gtgcggcgac    4140
gatagtcatg ccccgcgccc accggaagga gctgactggg ttgaaggctc tcaagggcat    4200
cggtcgacgc tctcccttat gcgactcctg cattaggaag cagcccagta gtaggttgag    4260
gccgttgagc accgccgccg caaggaatgg tgcatgcaag gagatggcgc ccaacagtcc    4320 cccgccacg gggcctgcca ccatacccac gccgaaacaa gcgctcatga gcccgaagtg     4380
gcgagcccga tcttccccat cggtgatgtc ggcgatatag gcgccagcaa ccgcacctgt    4440
ggcgccggtg atgccggcca cgatgcgtcc ggcgtagagg atccacagga cgggtgtggt    4500
cgccatgatc gcgtagtcga tagtggctcc aagtagcgaa gcgagcagga ctgggcggcg    4560
gccaaagcgg tcggacagtg ctccgagaac gggtgcgcat agaaattgca tcaacgcata    4620
```

```
tagcgctagc agcacgccat agtgactggc gatgctgtcg gaatggacga tatcccgcaa    4680
gaggcccggc agtaccggca taaccaagcc tatgcctaca gcatccaggg tgacggtgcc    4740
gaggatgacg atgagcgcat tgttagattt catacacggt gcctgactgc gttagcaatt    4800
taactgtgat aaactaccgc attaaagctt atcgatgata agctgtcaaa catgagacca    4860
tgggatatcg ctagcgacac catcgaatgg cgcaaaacct tcgcggtat ggcatgatag     4920 cgcccggaag agagtcaatt cagggtggtg aatgtgaaac cagtaacgtt atacgatgtc    4980
gcagagtatg ccggtgtctc ttatcagacc gtttccgcg tggtgaacca ggccagccac     5040
gtttctgcga aaacgcggga aaagtggaa gcggcgatgg cggagctgaa ttacattccc     5100
aaccgcgtgg cacaacaact ggcgggcaaa cagtcgttgc tgattggcgt tgccacctcc    5160
agtctggccc tgcacgcgcc gtcgcaaatt gtcgcggcga ttaaatctcg cgccgatcaa    5220
ctgggtgcca gcgtggtggt gtcgatggta gaacgaagcg cgtcgaagc ctgtaaagcg     5280 gcggtgcaca atcttctcgc gcaacgcgtc agtgggctga tcattaacta tccgctggat    5340
gaccaggatg ccattgctgt ggaagctgcc tgcactaatg ttccggcgtt atttcttgat    5400
gtctctgacc agacacccat caacagtatt attttctccc atgaagacgg tacgcgactg    5460
ggcgtggagc atctggtcgc attgggtcac cagcaaatcg cgctgttagc gggcccatta    5520
agttctgtct cggcgcgtct gcgtctggct ggctggcata atatctcac tcgcaatcaa     5580 attcagccga tagcggaacg ggaaggcgac tggagtgcca tgtccggttt tcaacaaacc    5640
atgcaaatgc tgaatgaggg catcgttccc actgcgatgc tggttgccaa cgatcagatg    5700
gcgctgggcg caatgcgcgc cattaccgag tccgggctgc gcgttggtgc ggatatctcg    5760
gtagtgggat acgacgatac cgaagacagc tcatgttata tcccgccgtt aaccaccatc    5820
aaacaggatt ttcgcctgct ggggcaaacc agcgtggacc gcttgctgca actctctcag    5880
ggccaggcgg tgaagggcaa tcagctgttg cccgtctcac tggtgaaaag aaaaaccacc    5940
ctggcgccca atacgcaaac cgcctctccc cgcgcgttgg ccgattcatt aatgcagctg    6000
gcacgacagg tttcccgact ggaaagcggg cagtgagcta gcgggaataa gggcgacacg    6060
gaaatgttga atactcatac tcttcctttt tcaatattat tgaagcattt atcagggtta    6120
ttgtctcatg agcggataca tatttgaatg tatttagaaa aataaacaaa taggggttcc    6180
gcgcacattt ccccgaaaag tgccacctga cgtctaagaa accattatta tcatgacatt    6240
aacctataaa aataggcgta tcacgaggcc ctttcgtctc gcgcgtttcg gtgatgacgg    6300
tgaaaacctc tgacacatgc agctcccgga cggtcaca gcttgtctgt aagcggatgc      6360
cgggagcaga caagcccgtc agggcgcgtc agcgggtgtt ggcgggtgtc ggggctggct    6420
taactatgcg gcatcagagc agattgtact gagagtgcac catatgctcg atggctacga    6480
gggcagacag taagtggatt taccataatc ccttaattgt acgcaccgct aaaacgcgtt    6540
cagcgcgatc acggcagcag acaggtaaaa atgcaacaa accacccgaa aaactgcgcc     6600
gatcgcgcct gataaatttt aaccgtatga ataccatgc aaccagaggg tacaggccac     6660
attaccccca cttaatccac tgaagctgcc atttttcatg gtttcaccat atgcggtgtg    6720
aaataccgca cagatgcgta aggagaaaat accgcatcag cgccattcg ccattcaggc     6780 tgcgcaactg ttgggaaggg cgatcggtgc gggcctcttc gctattacgc cagctggcga    6840 aaggggatg tgctgcaagg cgattaagtt gggtaacgcc agggttttcc cagtcacgac     6900
gttgtaaaac gacggccagt                                                 6920
```

<210> SEQ ID NO 31
<211> LENGTH: 25
<212> TYPE: DNA
<213> ORGANISM: Artificial Sequence
<220> FEATURE:
<223> OTHER INFORMATION: Primer

<400> SEQUENCE: 31
acgtgagttt cgttccact gagcg                                          25

<210> SEQ ID NO 32
<211> LENGTH: 20
<212> TYPE: DNA
<213> ORGANISM: Artificial Sequence
<220> FEATURE:
<223> OTHER INFORMATION: Primer

<400> SEQUENCE: 32
gggcccgata tcgccgtccc                                               20

<210> SEQ ID NO 33
<211> LENGTH: 4071
<212> TYPE: DNA
<213> ORGANISM: Artificial Sequence
<220> FEATURE:
<223> OTHER INFORMATION: Expression vector

<400> SEQUENCE: 33
gaattggaaa ttaatacgac tcactatagg ggaattgtga gcggataaca attcccctct    60
agaaataatt tgtttaact ttaagaagga gagaattcga gctcggtacc cggggatcct    120
ctagagtcga cctgcaggca tgcaagcttg actcctgttg atagatccag taatgacctc    180
agaactccat ctggatttgt tcagaacgct cggttgccgc cgggcgtttt ttattggtga    240
gaatacatgt gagcaaaagg ccagcaaaag gccaggaacc gtaaaaaggc cgcgttgctg    300 gcgttttcc ataggctccg ccccctgac gagcatcaca aaaatcgacg ctcaagtcag    360
aggtggcgaa acccgacagg actataaaga taccaggcgt ttcccctgg aagctccctc    420 gtgcgctctc ctgttccgac cctgccgctt accggatacc tgtccgcctt ctcccttcg    480 ggaagcgtgg cgctttctca tagctcacgc tgtaggtatc tcagttcggt gtaggtcgtt    540
cgctccaagc tgggctgtgt gcacgaaccc cccgttcagc ccgaccgctg cgccttatcc    600
ggtaactatc gtcttgagtc aacccggta agacacgact tatcgccact ggcagcagcc    660
actggtaaca ggattagcag agcgaggtat gtaggcggtg ctacagagtt cttgaagtgg    720
tggcctaact acggctacac tagaaggaca gtatttggta tctgcgctct gctgaagcca    780
gttaccttcg gaaaaagagt tggtagctct tgatccggca acaaaccac cgctggtagc    840 ggtggttttt ttgtttgcaa gcagcagatt acgcgcagaa aaaaggatc tcaagaagat    900 cctttgatct tttctacggg gtctgacgct cagtggaacg aaaactcacg tgggcccgat    960
atcgccgtcc cgtcaagtca gcgtaatgct ctgccagtgt tacaaccaat taaccaattc    1020
tgattagaaa aactcatcga gcatcaaatg aaactgcaat ttattcatat caggattatc    1080
aataccatat ttttgaaaaa gccgtttctg taatgaagga gaaaactcac cgaggcagtt    1140
ccataggatg gcaagatcct ggtatcggtc tgcgattccg actcgtccaa catcaataca    1200
acctattaat ttcccctcgt caaaaataag gttatcaagt gagaaatcac catgagtgac    1260
gactgaatcc ggtgagaatg gcaaaagctt atgcatttct ttccagactt gttcaacagg    1320
ccagccatta cgctcgtcat caaaatcact cgcatcaacc aaaccgttat tcattcgtga    1380

```
ttgcgcctga gcgagacgaa atacgcgatc gctgttaaaa ggacaattac aaacaggaat    1440
cgaatgcaac cggcgcagga acactgccag cgcatcaaca atattttcac ctgaatcagg    1500
atattcttct aatacctgga atgctgtttt cccggggatc gcagtggtga gtaaccatgc    1560
atcatcagga gtacgcataa aatgcttgat ggtcggaaga ggcataaatt ccgtcagcca    1620
gtttagtctg accatctcat ctgtaacatc attggcaacg ctaccttttgc catgtttcag    1680 aaacaactct ggcgcatcgg gcttcccata caatcgatag attgtcgcac ctgattgccc    1740
gacattatcg cgagcccatt tatacccata taaatcagca tccatgttgg aatttaatcg    1800
cggcctcgag caagacgttt cccgttgaat atggctcata cacccccttg tattactgtt    1860
tatgtaagca gacagttttta ttgttcatga tgatatattt ttatcttgtg caatgtaaca    1920
tcagagattt tgagacacac aacgtggcca attgtcagaa ttggttaatt ggttgtaaca    1980
ctggcagagc attacgctga cttgacggga cggcgatatc gctagcgaca ccatcgaatg    2040
gcgcaaaacc tttcgcggta tggcatgata gcgcccggaa gagagtcaat tcagggtggt    2100
gaatgtgaaa ccagtaacgt tatacgatgt cgcagagtat gccggtgtct cttatcagac    2160
cgtttcccgc gtggtgaacc aggccagcca cgtttctgcg aaaacgcggg aaaaagtgga    2220
agcggcgatg gcggagctga attacattcc caaccgcgtg gcacaacaac tggcgggcaa    2280
acagtcgttg ctgattggcg ttgccacctc cagtctggcc ctgcacgcgc cgtcgcaaat    2340
tgtcgcggcg attaaatctc gcgccgatca actgggtgcc agcgtggtgg tgtcgatggt    2400
agaacgaagc ggcgtcgaag cctgtaaagc ggcggtgcac aatcttctcg cgcaacgcgt    2460
cagtgggctg atcattaact atccgctgga tgaccaggat gccattgctg tggaagctgc    2520
ctgcactaat gttccggcgt tatttcttga tgtctctgac cagacaccca tcaacagtat    2580
tattttctcc catgaagacg gtacgcgact gggcgtggag catctggtcg cattgggtca    2640
ccagcaaatc gcgctgttag cgggcccatt aagttctgtc tcggcgcgtc tgcgtctggc    2700
tggctggcat aaatatctca ctcgcaatca aattcagccg atagcggaac gggaaggcga    2760
ctggagtgcc atgtccggtt ttcaacaaac catgcaaatg ctgaatgagg gcatcgttcc    2820
cactgcgatg ctggttgcca acgatcagat ggcgctgggc gcaatgcgcg ccattaccga    2880
gtccgggctg cgcgttggtg cggatatctc ggtagtggga tacgacgata ccgaagacag    2940
ctcatgttat atcccgccgt taaccaccat caaacaggat tttcgcctgc tggggcaaac    3000
cagcgtggac cgcttgctgc aactctctca gggccaggcg gtgaagggca atcagctgtt    3060
gcccgtctca ctggtgaaaa gaaaaaccac cctggcgccc aatacgcaaa ccgcctctcc    3120
ccgcgcgttg ccgattcat taatgcagct ggcacgacag gtttcccgac tggaaagcgg    3180
gcagtgagct agcgggaata aaggcgacac ggaaatgttg aatactcata ctcttccttt    3240
ttcaatatta ttgaagcatt tatcagggtt attgtctcat gagcggatac atatttgaat    3300
gtatttagaa aaataaacaa ataggggttc gcgcacatt tccccgaaaa gtgccacctg    3360
acgtctaaga aaccattatt atcatgacat taacctataa aaataggcgt atcacgaggc    3420
cctttcgtct cgcgcgtttc ggtgatgacg gtgaaaacct ctgacacatg cagctcccgg    3480
agacggtcac agcttgtctg taagcggatg ccggagcag acaagcccgt cagggcgcgt    3540
cagcgggtgt tggcgggtgt cggggctggc ttaactatgc ggcatcagag cagattgtac    3600
tgagagtgca ccatatgctc gatggctacg agggcagaca gtaagtggat ttaccataat    3660
cccttaattg tacgcaccgc taaaacgcgt tcagcgcgat cacggcagca gacaggtaaa    3720
```

```
aatggcaaca aaccacccga aaaactgccg cgatcgcgcc tgataaattt taaccgtatg      3780 aataccctatg caaccagagg gtacaggcca cattaccccc acttaatcca ctgaagctgc     3840
```


```
aatggcaaca aaccacccga aaaactgccg cgatcgcgcc tgataaattt taaccgtatg      3780 aataccctatg caaccagagg gtacaggcca cattaccccc acttaatcca ctgaagctgc     3840 cattttcat ggtttcacca tatgcggtgt gaaataccgc acagatgcgt aaggagaaaa       3900
taccgcatca ggcgccattc gccattcagg ctgcgcaact gttgggaagg gcgatcggtg      3960
cgggcctctt cgctattacg ccagctggcg aaaggggggat gtgctgcaag gcgattaagt    4020
tgggtaacgc cagggttttc ccagtcacga cgttgtaaaa cgacggccag t              4071
```

<210> SEQ ID NO 34
<211> LENGTH: 50
<212> TYPE: DNA
<213> ORGANISM: Artificial Sequence
<220> FEATURE:
<223> OTHER INFORMATION: Primer

<400> SEQUENCE: 34
aaaggatcca aactcgagag gtacgattta ctaactggaa gaggcactaa       50

<210> SEQ ID NO 35
<211> LENGTH: 26
<212> TYPE: DNA
<213> ORGANISM: Artificial Sequence
<220> FEATURE:
<223> OTHER INFORMATION: Primer

<400> SEQUENCE: 35
aaaaagcttt acgcgaacgc gaagtc       26

<210> SEQ ID NO 36
<211> LENGTH: 66
<212> TYPE: DNA
<213> ORGANISM: Artificial Sequence
<220> FEATURE:
<223> OTHER INFORMATION: Primer

<400> SEQUENCE: 36
aaaggatcca cagtcctgct aaaacgttcg tttgatatca ttttttcctga caccatcgaa       60 tggcgc       66

<210> SEQ ID NO 37
<211> LENGTH: 77
<212> TYPE: DNA
<213> ORGANISM: Artificial Sequence
<220> FEATURE:
<223> OTHER INFORMATION: Primer

<400> SEQUENCE: 37
aaactcgagt tcctgtgtga aattgttatc cgctcacaat tccacacatt atacgagccg       60
tcactgcccg ctttcca       77

<210> SEQ ID NO 38
<211> LENGTH: 30
<212> TYPE: DNA
<213> ORGANISM: Artificial Sequence
<220> FEATURE:
<223> OTHER INFORMATION: Primer

<400> SEQUENCE: 38
aaaaagcttg cgattgtgta ggctggagct       30

<210> SEQ ID NO 39
<211> LENGTH: 72

```
<212> TYPE: DNA
<213> ORGANISM: Artificial Sequence
<220> FEATURE:
<223> OTHER INFORMATION: Primer

<400> SEQUENCE: 39
aaaaagcttt aaaactaacc gggcgatgcg tcaatggcct tgtgaatccc atggtccata      60
tgaatatcct cc                                                         72

<210> SEQ ID NO 40
<211> LENGTH: 73
<212> TYPE: DNA
<213> ORGANISM: Artificial Sequence
<220> FEATURE:
<223> OTHER INFORMATION: Primer

<400> SEQUENCE: 40
aattggatcc acagtcctgc taaaacgttc gtttgatatc attttccctg acaccatcga      60
atggcgcaaa acc                                                        73

<210> SEQ ID NO 41
<211> LENGTH: 32
<212> TYPE: DNA
<213> ORGANISM: Artificial Sequence
<220> FEATURE:
<223> OTHER INFORMATION: Primer

<400> SEQUENCE: 41
aattcaattg agactcgtgc aactggtcag cg                                    32

<210> SEQ ID NO 42
<211> LENGTH: 9023
<212> TYPE: DNA
<213> ORGANISM: Artificial Sequence
<220> FEATURE:
<223> OTHER INFORMATION: DNA plasmid with T7 expression construct

<400> SEQUENCE: 42
aaaggatcca cagtcctgct aaaacgttcg tttgatatca ttttcctga caccatcgaa       60 tggcgcaaaa cctttcgcgg tatggcatga tagcgcccgg aagagagtca attcagggtg     120
gtgaatgtga aaccagtaac gttatacgat gtcgcagagt atgccggtgt ctcttatcag     180
accgtttccc gcgtggtgaa ccaggccagc cacgtttctg cgaaaacgcg ggaaaaagtg     240
gaagcggcga tggcggagct gaattacatt cccaaccgcg tggcacaaca actggcgggc     300
aaacagtcgt tgctgattgg cgttgccacc tccagtctgg ccctgcacgc gccgtcgcaa     360
attgtcgcgg cgattaaatc tcgcgccgat caactgggtg ccagcgtggt ggtgtcgatg     420
gtagaacgaa gcggcgtcga agcctgtaaa gcggcggtgc acaatcttct cgcgcaacgc     480
gtcagtgggc tgatcattaa ctatccgctg gatgaccagg atgccattgc tgtggaagct     540
gcctgcacta atgttccggc gttatttctt gatgtctctg accagacacc catcaacagt     600
attattttct cccatgaaga cggtacgcga ctgggcgtgg agcatctggt cgcattgggt     660
caccagcaaa tcgcgctgtt agcgggccca ttaagttctg tctcggcgcg tctgcgtctg     720
gctggctggc ataaatatct cactcgcaat caaattcagc cgatagcgga acgggaaggc     780
gactggagtg ccatgtccgg ttttcaacaa accatgcaaa tgctgaatga gggcatcgtt     840
cccactgcga tgctggttgc caacgatcag atggcgctgg gcgcaatgcg cgccattacc     900
gagtccgggc tgcgcgttgg tgcggatatc tcggtagtgg gatacgacga taccgaagac     960
```

```
agctcatgtt atatcccgcc gttaaccacc atcaaacagg attttcgcct gctgggcaa      1020 accagcgtgg accgcttgct gcaactctct cagggccagg cggtgaaggg caatcagctg      1080
ttgcccgtct cactggtgaa agaaaaaacc accctggcgc ccaatacgca aaccgcctct      1140
ccccgcgcgt tggccgattc attaatgcag ctggcacgac aggtttcccg actggaaagc      1200
gggcagtgag cgcaacgcaa ttaatgtaag ttagctcact cattaggcac cccaggcttt      1260
acactttatg cttccggctc gtataatgtg tggaattgtg agcggataac aatttcacac      1320
aggaaacagc tatgaccatg attacggatt cactggccgt cgttttacaa cgtcgtgact      1380
gggaaaaccc tggcgttacc caacttaatc gccttgcagc acatccccct ttcgccagct      1440
ggcgtaatag cgaagaggcc cgcaccgatc gcccttccca acagttgcgc agcctgaatg      1500
gcgaatggcg ctttgcctgg tttccggcac cagaagcggt gccggaaagc tggctggagt      1560
gcgatcttcc tgaggccgat actgtcgtcg tcccctcaaa ctggcagatg cacggttacg      1620
atgcgcccat ctacaccaac gtgacctatc ccattacggt caatccgccg tttgttccca      1680
cggagaatcc gacgggttgt tactcgctca catttaatgt tgatgaaagc tggctacagg      1740
aaggccagac gcgaattatt tttgatggcg tcgggatctg atccggattt actaactgga      1800
agaggcacta aatgaaacgg attaacatcg ctaagaacga cttctctgac atcgaactgg      1860
ctgctatccc gttcaacact ctggctgacc attacggtga gcgtttagct cgcgaacagt      1920
tggcccttga gcatgagtct tacgagatgg gtgaagcacg cttccgcaag atgtttgagc      1980
gtcaacttaa agctggtgag gttgcggata cgctgccgc caagcctctc atcactaccc      2040
tactccctaa gatgattgca cgcatcaacg actggtttga ggaagtgaaa gctaagcgcg      2100
gcaagcgccc gacagccttc cagttcctgc aagaaatcaa gccggaagcc gtagcgtaca      2160
tcaccattaa gaccactctg gcttgcctaa ccagtgctga caatacaacc gttcaggctg      2220
tagcaagcgc aatcggtcgg gccattgagg acgaggctcg cttcggtcgt atccgtgacc      2280
ttgaagctaa gcacttcaag aaaaacgttg aggaacaact caacaagcgc gtagggcacg      2340
tctacaagaa agcatttatg caagttgtcg aggctgacat gctctctaag ggtctactcg      2400
gtggcgaggc gtggtcttcg tggcataagg aagactctat tcatgtagga gtacgctgca      2460
tcgagatgct cattgagtca accggaatgg ttagcttaca ccgccaaaat gctggcgtag      2520
taggtcaaga ctctgagact atcgaactcg cacctgaata cgctgaggct atcgcaaccc      2580
gtgcaggtgc gctggctggc atctctccga tgttccaacc ttgcgtagtt cctcctaagc      2640
cgtggactgg cattactggt ggtggctatt ggctaacgg tcgtcgtcct ctggcgctgg      2700
tgcgtactca cagtaagaaa gcactgatgc gctacgaaga cgtttacatg cctgaggtgt      2760
acaaagcgat taacattgcg caaaacaccg catggaaaat caacaagaaa gtcctagcgg      2820
tcgccaacgt aatcaccaag tggaagcatt gtccggtcga ggacatccct gcgattgagc      2880
gtgaagaact cccgatgaaa ccggaagaca tcgacatgaa tcctgaggct ctcaccgcgt      2940
ggaaacgtgc tgccgctgct gtgtaccgca aggacaaggc tcgcaagtct cgccgtatca      3000
gccttgagtt catgcttgag caagccaata gtttgctaa ccataaggcc atctggttcc      3060
cttacaacat ggactggcgc ggtcgtgttt acgctgtgtc aatgttcaac ccgcaaggta      3120
acgatatgac caaaggactg cttacgctgg cgaaggtaa accaatcggt aaggaaggtt      3180
actactggct gaaaatccac ggtgcaaact gtgcgggtgt cgataaggtt ccgttccctg      3240
agcgcatcaa gttcattgag gaaaaccacg agaacatcat ggcttgcgct aagtctccac      3300
tggagaacac ttggtgggct gagcaagatt ctccgttctg cttccttgcg ttctgctttg      3360
```

```
agtacgctgg ggtacagcac cacggcctga gctataactg ctcccttccg ctggcgtttg   3420
acgggtcttg ctctggcatc cagcacttct ccgcgatgct ccgagatgag gtaggtggtc   3480
gcgcggttaa cttgcttcct agtgaaaccg ttcaggacat ctacgggatt gttgctaaga   3540
aagtcaacga gattctacaa gcagacgcaa tcaatgggac cgataacgaa gtagttaccg   3600
tgaccgatga gaacactggt gaaatctctg agaaagtcaa gctgggcact aaggcactgg   3660
ctggtcaatg gctggcttac ggtgttactc gcagtgtgac taagcgttca gtcatgacgc   3720
tggcttacgg gtccaaagag ttcggcttcc gtcaacaagt gctggaagat accattcagc   3780
cagctattga ttccggcaag ggtctgatgt tcactcagcc gaatcaggct gctggataca   3840
tggctaagct gatttgggaa tctgtgagcg tgacggtggt agctgcggtt gaagcaatga   3900
actggcttaa gtctgctgct aagctgctgg ctgctgaggc caaagataag aagactggag   3960
agattcttcg caagcgttgc gctgtgcatt gggtaactcc tgatggtttc cctgtgtggc   4020
aggaatacaa gaagcctatt cagacgcgct gaacctgat gttcctcggt cagttccgct   4080
tacagcctac cattaacacc aacaaagata gcgagattga tgcacacaaa caggagtctg   4140
gtatcgctcc taactttgta cacagccaag acggtagcca ccttcgtaag actgtagtgt   4200
gggcacacga gaagtacgga atcgaatctt ttgcactgat tcacgactcc ttcggtacca   4260
ttccggctga cgctgcgaac ctgttcaaag cagtgcgcga aactatggtt gacacatatg   4320
agtcttgtga tgtactggct gatttctacg accagttcgc tgaccagttg cacgagtctc   4380
aattggacaa aatgccagca cttccggcta aaggtaactt gaacctccgt gacatcttag   4440
agtcggactt cgcgttcgcg taaaagcttg cgattgtgta ggctggagct gcttcgaagt   4500
tcctatactt tctagagaat aggaacttcg gaataggaac ttcaagatcc cctcacgctg   4560
ccgcaagcac tcagggcgca agggctgcta aaggaagcgg aacacgtaga aagccagtcc   4620
gcagaaacgg tgctgacccc ggatgaatgt cagctactgg gctatctgga caagggaaaa   4680
cgcaagcgca aagagaaagc aggtagcttg cagtgggctt acatggcgat agctagactg   4740
ggcggtttta tggacagcaa gcgaaccgga attgccagct ggggcgccct ctggtaaggt   4800
tgggaagccc tgcaaagtaa actggatggc tttcttgccg ccaaggatct gatggcgcag   4860
gggatcaaga tctgatcaag agacaggatg aggatcgttt cgcatgattg aacaagatgg   4920
attgcacgca ggttctccgg ccgcttgggt ggagaggcta ttcggctatg actgggcaca   4980
acagacaatc ggctgctctg atgccgccgt gttccggctg tcagcgcagg ggcgcccggt   5040 tcttttttgtc aagaccgacc tgtccggtgc cctgaatgaa ctgcaggacg aggcagcgcg   5100
gctatcgtgg ctggccacga cgggcgttcc ttgcgcagct gtgctcgacg ttgtcactga   5160
agcgggaagg gactggctgc tattgggcga agtgccgggg caggatctcc tgtcatctca   5220
ccttgctcct gccgagaaag tatccatcat ggctgatgca atgcggcggc tgcatacgct   5280
tgatccggct acctgcccat tcgaccacca agcgaaacat cgcatcgagc gagcacgtac   5340
tcggatggaa gccggtcttg tcgatcagga tgatctggac gaagagcatc aggggctcgc   5400
gccagccgaa ctgttcgcca ggctcaaggc gcgcatgccc gacggcgagg atctcgtcgt   5460
gacccatggc gatgcctgct tgccgaatat catggtggaa aatggccgct tttctggatt   5520
catcgactgt ggccggctgg gtgtggcgga ccgctatcag gacatagcgt tggctacccg   5580
tgatattgct gaagagcttg gcggcgaatg ggctgaccgc ttcctcgtgc tttacggtat   5640
cgccgctccc gattcgcagc gcatcgcctt ctatcgcctt cttgacgagt tcttctgagc   5700
```

```
gggactctgg ggttcgaaat gaccgaccaa gcgacgccca acctgccatc acgagatttc    5760
gattccaccg ccgccttcta tgaaaggttg ggcttcggaa tcgttttccg ggacgccggc    5820
tggatgatcc tccagcgcgg ggatctcatg ctggagttct tcgcccaccc cagcttcaaa    5880
agcgctctga agttcctata ctttctagag aataggaact tcggaatagg aactaaggag    5940
gatattcata tggaccatgg gattcacaag gccattgacg catcgcccgg ttagttttaa    6000 agcttttat cactagtgaa ttcgcggccg cctgcaggtc gaccatatgg gagagctccc     6060
aacgcgttgg atgcatagct tgagtattct atagtgtcac ctaaatagct tggcgtaatc    6120
atggtcatag ctgtttcctg tgtgaaattg ttatccgctc acaattccac acaacatacg    6180
agccggaagc ataaagtgta aagcctgggg tgcctaatga gtgagctaac tcacattaat    6240
tgcgttgcgc tcactgcccg ctttccagtc gggaaacctg tcgtgccagc tgcattaatg    6300
aatcggccaa cgcgcgggga gaggcggttt gcgtattggg cgctcttccg cttcctcgct    6360
cactgactcg ctgcgctcgg tcgttcggct gcggcgagcg gtatcagctc actcaaaggc    6420
ggtaatacgg ttatccacag aatcagggga taacgcagga aagaacatgt gagcaaaagg    6480
ccagcaaaag gccaggaacc gtaaaaaggc cgcgttgctg gcgtttttcc ataggctccg    6540
cccccctgac gagcatcaca aaaatcgacg ctcaagtcag aggtggcgaa acccgacagg    6600
actataaaga taccaggcgt ttccccctgg aagctccctc gtgcgctctc ctgttccgac    6660
cctgccgctt accggatacc tgtccgcctt tctcccttcg ggaagcgtgg cgctttctca    6720
tagctcacgc tgtaggtatc tcagttcggt gtaggtcgtt cgctccaagc tgggctgtgt    6780
gcacgaaccc cccgttcagc ccgaccgctg cgccttatcc ggtaactatc gtcttgagtc    6840
caacccggta agacacgact tatcgccact ggcagcagcc actggtaaca ggattagcag    6900
agcgaggtat gtaggcggtg ctacagagtt cttgaagtgg tggcctaact acggctacac    6960
tagaagaaca gtatttggta tctgcgctct gctgaagcca gttaccttcg gaaaaagagt    7020
tggtagctct tgatccggca aacaaaccac cgctggtagc ggtggttttt ttgtttgcaa    7080
gcagcagatt acgcgcagaa aaaaaggatc tcaagaagat cctttgatct tttctacggg    7140
gtctgacgct cagtggaacg aaaactcacg ttaagggatt ttggtcatga gattatcaaa    7200
aaggatcttc acctagatcc ttttaaatta aaaatgaagt tttaaatcaa tctaaagtat    7260
atatgagtaa acttggtctg acagttacca atgcttaatc agtgaggcac ctatctcagc    7320
gatctgtcta tttcgttcat ccatagttgc ctgactcccc gtcgtgtaga taactacgat    7380
acgggagggc ttaccatctg gccccagtgc tgcaatgata ccgcgagacc cacgctcacc    7440
ggctccagat ttatcagcaa taaaccagcc agccggaagg gccgagcgca gaagtggtcc    7500
tgcaacttta tccgcctcca tccagtctat taattgttgc cgggaagcta gagtaagtag    7560
ttcgccagtt aatagtttgc gcaacgttgt tgccattgct acaggcatcg tggtgtcacg    7620
ctcgtcgttt ggtatggctt cattcagctc cggttcccaa cgatcaaggc gagttacatg    7680
atcccccatg ttgtgcaaaa aagcggttag ctccttcggt cctccgatcg ttgtcagaag    7740
taagttggcc gcagtgttat cactcatggt tatggcagca ctgcataatt ctcttactgt    7800
catgccatcc gtaagatgct tttctgtgac tggtgagtac tcaaccaagt cattctgaga    7860
atagtgtatg cggcgaccga gttgctcttg cccggcgtca atacgggata ataccgcgcc    7920
acatagcaga actttaaaag tgctcatcat tggaaaacgt tcttcggggc gaaaactctc    7980
aaggatctta ccgctgttga gatccagttc gatgtaaccc actcgtgcac ccaactgatc    8040
ttcagcatct tttactttca ccagcgtttc tgggtgagca aaaacaggaa ggcaaaatgc    8100
```

```
cgcaaaaaag ggaataaggg cgacacggaa atgttgaata ctcatactct tccttttca    8160 atattattga agcatttatc agggttattg tctcatgagc ggatacatat ttgaatgtat    8220
ttagaaaaat aaacaaatag gggttccgcg cacatttccc cgaaaagtgc cacctgatgc    8280
ggtgtgaaat accgcacaga tgcgtaagga gaaataccg catcaggaaa ttgtaagcgt     8340
taatattttg ttaaaattcg cgttaaattt ttgttaaatc agctcatttt ttaaccaata    8400
ggccgaaatc ggcaaaatcc cttataaatc aaaagaatag accgagatag ggttgagtgt    8460
tgttccagtt tggaacaaga gtccactatt aaagaacgtg gactccaacg tcaaagggcg    8520
aaaaaccgtc tatcagggcg atggcccact acgtgaacca tcaccctaat caagtttttt    8580
ggggtcgagg tgccgtaaag cactaaatcg aaccctaaa gggagccccc gatttagagc     8640
ttgacgggga aagccggcga acgtggcgag aaaggaaggg aagaaagcga aaggagcggg    8700
cgctagggcg ctggcaagtg tagcggtcac gctgcgcgta accaccacac ccgccgcgct    8760
taatgcgccg ctacgggcg cgtccattcg ccattcaggc tgcgcaactg ttgggaaggg     8820
cgatcggtgc gggcctcttc gctattacgc cagctggcga aaggggggatg tgctgcaagg   8880 cgattaagtt gggtaacgcc agggttttcc cagtcacgac gttgtaaaac gacggccagt    8940
gaattgtaat acgactcact atagggcgaa ttgggcccga cgtcgcatgc tcccggccgc    9000
catggcggcc gcgggaattc gat                                            9023

<210> SEQ ID NO 43
<211> LENGTH: 39
<212> TYPE: DNA
<213> ORGANISM: Escherichia coli

<400> SEQUENCE: 43
acagtcctgc taaaacgttc gtttgatatc attttttcct                          39

<210> SEQ ID NO 44
<211> LENGTH: 39
<212> TYPE: DNA
<213> ORGANISM: Escherichia coli

<400> SEQUENCE: 44
gattcacaag gccattgacg catcgcccgg ttagtttta                           39
```

T7 EXPRESSION SYSTEM, METHOD FOR ITS PRODUCTION AND USE THEREOF FOR PRODUCING RECOMBINANT PROTEINS

BACKGROUND OF THE INVENTION

The invention relates to a T7 expression system, method for its production and use thereof for antibiotic-free production of recombinant proteins.

T7 expression systems are used for the expression of recombinant proteins. As a rule the T7 promoter sequence is located on a vector and the coding region for a recombinant protein downstream therefrom after a ribosome binding site. Since no T7 polymerase is produced by the expression organism, such an expression system is only functional when the T7 polymerase has been artificially introduced into the system. The commonest method for this is the genomic anchoring of a T7 expression cassette in the production organism. A T7 polymerase-based prokaryotic system for the expression of proteins in BL21 (DE3) *Escherichia coli* cells has long been known. In this system, the integration of the T7 polymerase into the *E. coli* genome takes place with the aid of the DE3 lambda phage into the lambda attachment site of *E. coli*. In the system, the T7 phage polymerase recognizes the T7 phage promoter. However, this system has the disadvantage that the plasmid stability during target gene expression is low. Numerous studies have attempted to stabilize the expression level of the T7 expression system, but so far without appreciable success. Moreover, *E. coli* contains ca. 40 kb lambda phage DNA. This phage DNA is undesired, at least in systems for the expression of pharmaceutical proteins. Furthermore, in T7 expression systems expression vectors which contain an antibiotic resistance gene as selection marker for the cloning and selection during the expression have always hitherto been used.

However, the use of antibiotics for the selection of plasmids is a critical disadvantage, particularly in the production of therapeutic proteins. An antibiotic-free method is more acceptable to the regulatory authorities, since the product will be safer for the patients and because of the minor end product analysis (elimination of the antibiotic in the product) a markedly more economical process can be constructed. An expression vector which enables a method for antibiotic-free production of proteins is for example known from EP1697523B1. However, this expression vector is not suitable for a T7 expression system.

DESCRIPTION OF THE INVENTION

The purpose of the present invention is to provide a T7 expression system for the antibiotic-free production of a recombinant protein consisting of a prokaryotic cell and an expression vector which displays increased stability of the expression vector in comparison to known T7 expression systems.

This problem is solved by an expression system comprising a prokaryotic cell containing a nucleotide construct coding for a T7 RNA polymerase under control of a T7 promoter and under control of an inducible promoter, and an expression vector which contains a gene encoding a recombinant protein to be expressed under the control of a T7 promoter, characterized in that the expression vector contains a plasmid stabilization system.

Plasmid stabilization systems are for example known from Sengupta and Austin, Infection and Immunity, July 2011, p. 2502-2509. Preferably it is a plasmid stabilization system from the group of multimer resolution systems (mrs), partitioning systems (par) and postsegregational killing systems (PSK). Particularly preferably the plasmid stabilization system contains a sequence from the group of the multimer resolution systems, and especially preferably this is the cer sequence.

The inducible promoter is preferably a promoter from the group tac, lac, trp and phoA. Particularly preferably it is the inducible promoter lacUV5.

The nucleotide construct is preferably a nucleotide construct consisting of the nucleotide sequence coding for the T7 RNA polymerase, the nucleotide sequence of the lacUV5 promoter including the 5' end of the lacZ gene from *E. coli* and the T7 promoter sequence. Such a nucleotide construct is reproduced in SEQ ID NO:1. Particularly preferably, the nucleotide construct is integrated into the genome of the prokaryotic cell of the expression system according to the invention.

The prokaryotic cell is preferably a cell of an *E. coli* strain with the T7 RNA polymerase gene in the genome. Such strains can be produced in a manner known per se from wild type strains such as are available in strain collections. Examples of such strains are the *E. coli* strains BL21 (commercially available from Stratagene, La Jolla USA) HMS174 (DSM5932), or C600 (DSM426) (available under said DSM numbers from the Deutschen Sammlung für Mikroorganismen und Zellkulturen GmbH (DSMZ) [German Collection of Microorganisms and Cell Cultures], 38124 Brauschweig, Inhoffenstraße 7B).

Preferably, the T7 expression system according to the invention is produced by introducing a T7 expression vector developed in the context of the present invention into these strains.

Such an expression vector according to the invention preferably has the following constituents in functional linkage:
a replication origin (ori),
a T7 promoter as regulatory sequence,
a sequence which codes for a recombinant protein to be expressed
an antibiotic resistance gene as selection marker for the cloning,
a terminator,
a repressor gene,
an operator sequence suitable for the repressor gene, and
a plasmid stabilization system.

Preferably it is one of the already mentioned plasmid stabilization systems. Particularly preferably the plasmid stabilization system contains the cer sequence.

Preferably the replication origin is the pBR322-ori, the pUC19-ori or the p15A-ori, particularly preferably the pBR322-ori.

Particularly preferably the terminator is $t_0$, rrnB or the T7 terminator.

A repressor gene is any gene which encodes a protein which on binding in the promoter region prevents the transcription of genes. Particularly preferably, the repressor gene is the lacI gene.

Preferably, the antibiotic resistance gene is kan, tet, bla, $cm^R$ or tetA, particularly preferably kan.

The T7 expression system according to the invention can be produced like already known T7 expression systems, with the difference that an expression vector according to the invention is introduced into a prokaryotic cell with a T7 RNA polymerase gene in the genome.

A further purpose of the invention is to provide a method for producing a preferred embodiment of a prokaryotic cell as part of the T7 expression system according to the invention, which effects the integration of the T7 RNA polymerase including the control regions into the prokaryotic cell, without integration of phage DNA into the cell occurring in the process.

This method is characterized in that the coding sequence of the T7 RNA polymerase including the control regions is integrated into the genome of the prokaryotic cell by means of a "site-specific" recombination.

Such a "site-specific" recombination is for example enabled by the Cre-lox system from the bacteriophage P1 and the FLP-FRT system from yeast. The use of "site-specific" recombination for modifications of chromosomal bacterial DNA is for example described in Datsenko and Wanner, PNAS, Jun. 6, 2000 no. 12, p. 6640-6645.

Preferably, the targeted integration of the T7 RNA polymerase is effected under control of an inducible promoter into a defined position in the E. coli genome, preferably the proBA sequence of E. coli. Such methods are for example known from Datsenko and Wanner, PNAS, Jun. 6, 2000 no. 12, p. 6640-6645.

A prokaryotic cell containing integrated into the genome a nucleotide construct coding for a T7 RNA polymerase under control of a T7 promoter and under control of an inducible promoter produced by this method differs from known prokaryotic cells which contain such a construct in that it contains no lambda phage DNA. Entirely surprisingly, it was found that in such cells conventional expression vectors also display increased stability, even though with the expression vectors according to the invention a still further increased stability can be achieved.

The invention thus also relates to a prokaryotic cell, preferably an E. coli cell, containing integrated into the genome a nucleotide construct coding for a T7 RNA polymerase under control of a T7 promoter and under control of an inducible promoter characterized in that it contains no lambda phage DNA.

Apart from this, the advantage of the present invention is its utilization in antibiotic-free fermentations in complex medium, whereby as a rule a higher expression efficiency of the protein to be produced can be achieved than with the use of mineral salt medium as with the expression system described in EP1697523B1. The invention thus also relates to a method for producing a recombinant protein by means of an expression system according to the invention.

This method is characterized in that the expression vector according to the invention is introduced into the prokaryotic cell containing a nucleotide construct coding for a T7 RNA polymerase under control of a T7 promoter and under control of an inducible promoter, these cells are fermented under antibiotic-free conditions which are suitable for the expression of the T7 RNA polymerase and the expression of the recombinant protein starting from a polynucleotide sequence, whereby the recombinant polypeptide is expressed and the recombinant polypeptide is isolated.

In the present invention, the fermentation process, i.e. the actual procedure for the expression of the protein, takes place in an entirely antibiotic-free environment. As a result, the problems mentioned at the start which are associated with the use of antibiotics for the selection of plasmids, for example reservations of the regulatory authorities, product safety, end product analysis (elimination of the antibiotic in the product) and the risks and costs associated therewith are avoided.

In the sense of the present invention, proteins are also to be understood to mean peptides and polypeptides.

The method according to the invention is preferably performed in a bioreactor.

The following examples serve for further illustration of the invention.

EXAMPLE 1

Production of Expression Vectors and Plasmids According to the Invention

Production of the Expression Plasmid pSCIL006c

Figure 3:
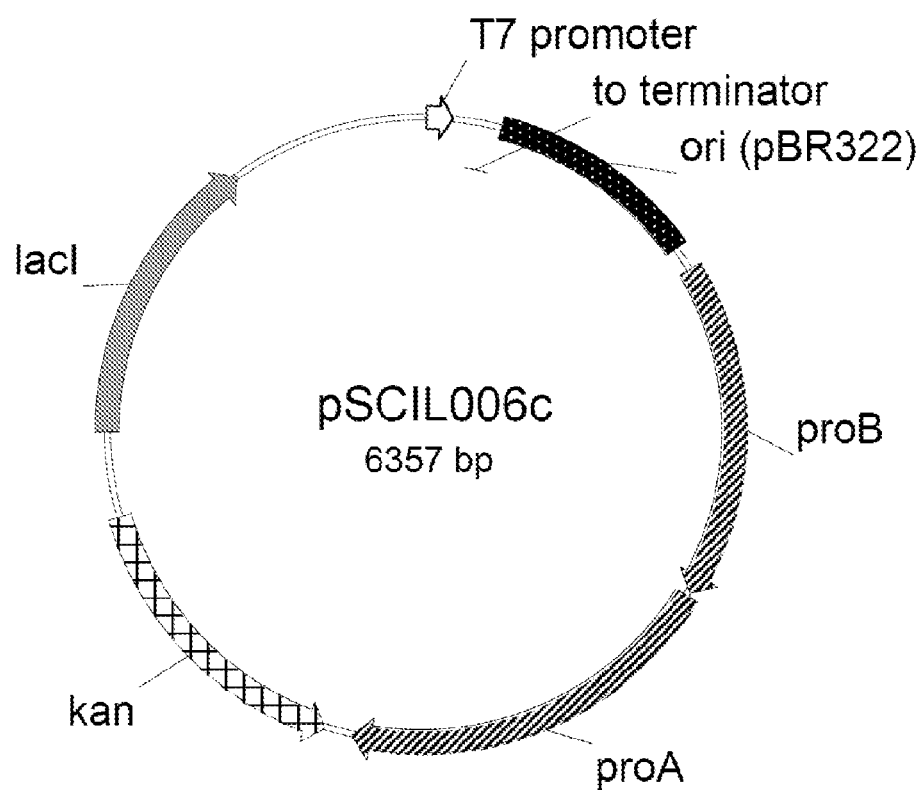
FIG. 3 schematically shows the expression vector pSCIL006c consisting of T7 promoter, t0 terminator, pBR322-ori, proBA, kan and lacI.

The production of the expression vector pSCIL006c (FIG. 3) is described in more detail below.

1. Insertion of the t0 Terminator into pUC19=pSCIL001

The commercially available vector pUC19 (SD0061, MBI Fermentas) was used as the basis for the production of the expression vector. pUC19 was cleaved with the endonucleases HindIII and AflIII, which resulted in the deletion of 359 bp of the vector sequence. The t0 transcription terminator was amplified from DNA of the phage lambda (SD0011, MBI Fermentas) by means of the primers t0-OD-MCS-HindIII (SEQ ID NO: 2) and t0-UU-MCS-AflIII (SEQ ID NO: 3). The fragment formed was then cleaved with the endonucleases HindIII and AflIII and after purification (Minielute Kit, Qiagen) cloned into the pUC19$^{HindIII/AflIII}$ fragment. The resulting plasmid pSCIL101 was checked by restriction analyses and sequencing.

2. Replacement of the Antibiotic Resistance Cassette in pSCIL001=pSCIL002

The kanamycin resistance cassette was amplified from pACYC177 (E4151 S, NEB) by PCR with the primers Km-OD-ApaI (SEQ ID NO: 4) and Km-UU-NheI (SEQ ID NO: 5). The fragment was purified with a Gel Extraction Kit (Qiagen) and cloned into pGEM-T easy (A1360, Promega). The plasmid pSCIL101 was amplified without the ampicillin resistance cassette by means of the primers pUC2541-OD-NheI (SEQ ID NO: 6) and pUC1496-UU-ApaI (SEQ ID NO: 7) and cleaved with the endonucleases ApaI and NheI. The kanamycin resistance cassette was cleaved from pGEMT-T easy with the endonucleases ApaI and NheI and cloned into pSCIL001 (ΔAmp)$^{ApaI/NheI}$. The resulting plasmid pSCIL002 was checked by restriction analyses.

3. Alteration of the Orientation of the Kanamycin Resistance Cassette=pSCIL002b The orientation of the kanamycin resistance cassette in pSCL vectors has a decisive role in the background expression of the kanamycin resistance gene, therefore the orientation of the resistance cassette in the second vector generation was altered in comparison to for example pSCIL008 (EP1697523B1). For this, the backbone of pSCIL002 was firstly amplified without kanamycin resistance cassette by means of the primers MunI-Km term (SEQ ID NO: 8) and ApaI-pSCIL002 (SEQ ID NO: 9) and then cleaved with the nucleases MunI (MfeI) and ApaI. The kanamycin resistance cassette was amplified with the primers Km 5'-MunI (SEQ ID NO: 10) and Km 3' ApaI (SEQ ID NO: 11) from pSCIL002 and likewise cleaved with the endonucleases MunI (MfeI) and ApaI. Both fragments were then ligated, which resulted in the plasmid pSCIL002b. Correct integration was checked by sequencing.

4. Insertion of a Second Selection Marker into pSCIL002b=pSCIL003b

The genes for the proline synthesis pathway of *E. coli*, proBA, were then integrated into pSCIL002b as a second selection marker. For this, firstly the proBA operon was amplified by means of the primers proBA-OD-ApaI (SEQ ID NO: 12) and proBA-UU-ApaI (SEQ ID NO: 13) from previously prepared genomic DNA from *E. coli* K12 (DSM 9037, Deutschen Sammlung für Mikro-organismen and Zellkulturen GmbH; DNeasy Tissue Kit, Qiagen). The PCR product was cleaved with the endonuclease ApaI and cloned into the vector pSCIL002b, likewise cleaved with ApaI. The resulting plasmid pSCIL003b was checked by sequencing.

5. Insertion of the Repressor Gene lacI into pSCIL003b=pSCIL004b

The lacI gene including the native promoter region was amplified from chromosomal DNA of the *E. coli* strain K12 (DSM 9037, Deutschen Sammlung fur Mikroorganismen and Zellkulturen GmbH; DNeasy Tissue Kit, Qiagen) by means of the primers lacI OD NheI (SEQ ID NO: 14) and lacI UU NheI (SEQ ID NO: 15). The PCR product was cloned into pGEM-T easy (A1360, Promega) and checked by sequencing. After restriction with the endonuclease NheI, lacI was ligated into pSCIL003b.

6. Insertion of the T7 Promoter into pSCIL004b=pSCIL006b

The T7 promoter including the lac operator sequence was amplified from the plasmid pSCIL006 (originally from pTYB2, #6710, NEB) by means of the primers PrT7-MunI5' (SEQ ID No: 16) and PrT7-EcoRI3' (SEQ ID NO: 17). In addition, by means of the primer PrT7-EcoRI3' the later ribosome binding site (AGGAGA) was integrated into the PCR product. The PCR product was cleaved with the endonucleases EcoRI and MunI (MfeI) and cloned into the vector pSCIL004b cleaved with EcoRI. The resulting plasmid pSCIL006b was checked by sequencing.

7. Alteration of the Replication Origin (Origin of Replication) by Replacement of One Nucleotide in pSCIL006b=pSCIL006c As a descendant of pUC19, the expression plasmid pSCIL006b shows a very much higher copy number at 37° C. than at 30° C. The reason for this is a point mutation (G→A) in the origin of replication of the original plasmid pBR322. To reverse this mutation in pSCIL006b, the Phusion Site Directed Mutagenesis Kit (F-541, Finnzymes) was used. For this, the whole plasmid was amplified with the primers ori_mut_fwd (SEQ ID NO: 18) and ori_rev (SEQ ID NO: 19) and religated. The resulting plasmid with a copy number which irrespective of the temperature lies at ca. 60 copies/cell, was checked by sequencing and designated as pSCIL006c (see FIG. 3, SEQ ID NO: 20).

Production of the Expression Vectors pSCIL122 and pSCIL123

1. Insertion of cer into pSCIL006c=pSCIL122 and pSCIL123

Figure 4:
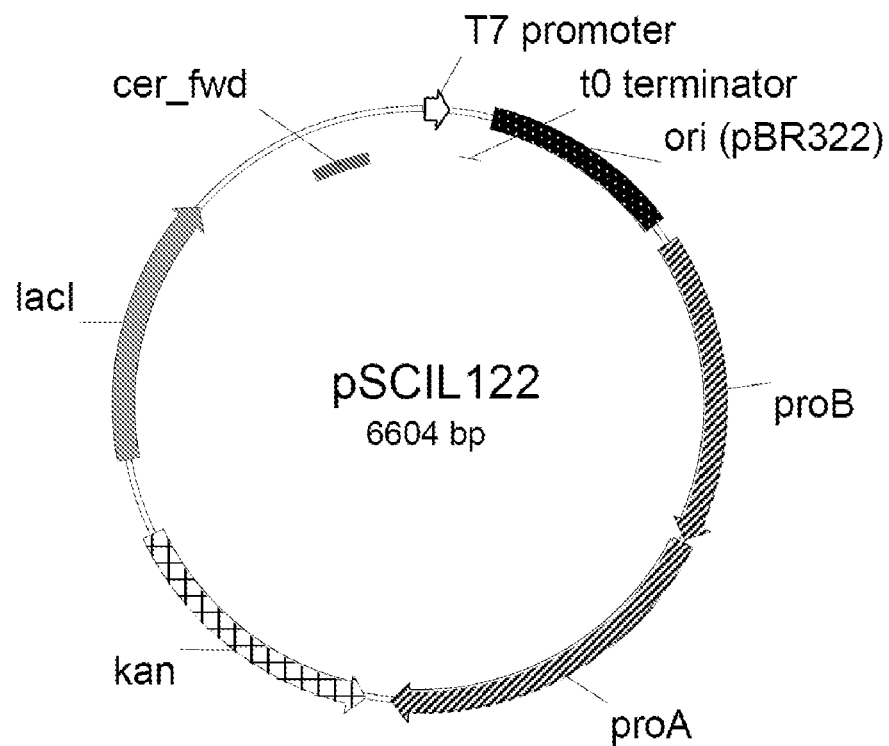
FIG. 4 schematically shows the expression vectors pSCIL122 and pSCIL123 consisting of T7 promoter, t0 terminator, pBR322-ori, proBA, kan, lacI and cer.
Figure 4:
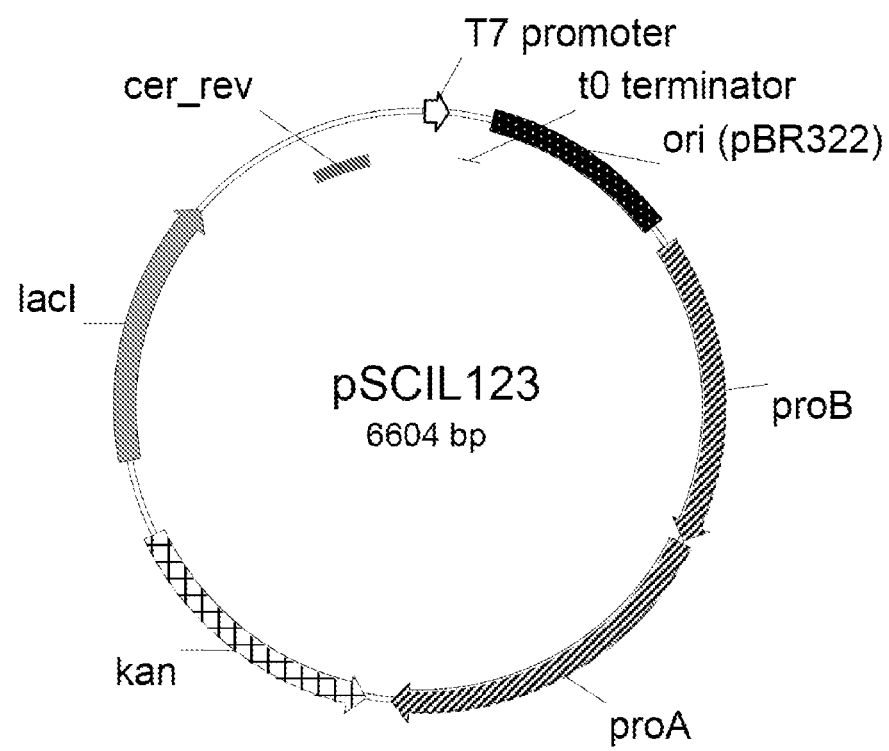

The cer element was amplified from the plasmid ColE1 (isolated from *E. coli* JC411 (DSM3877), DSMZ, by means of QIAprep Spin Miniprep, Qiagen) by PCR with the primers 5'cer_NdeI (SEQ ID NO: 21) and 3'cer_NdeI (SEQ ID NO: 22) and integrated into a unique NdeI cleavage site in pSCIL006c. In this, both orientations (forward and reverse) are possible. The resulting plasmid with cer in forward orientation was designated as pSCIL122, and the plasmid with cer in reverse orientation was designated as pSCIL123 and checked by sequencing (see FIG. 4, SEQ ID NO: 23).

Production of the Expression Vectors pSCIL124 and pSCIL125

1. Deletion of kan in pSCIL006c=pSCIL112

For the deletion of the kanamycin resistance cassette, the Phusion Site Directed Mutagenesis Kit (F-541, Finnzymes) was used. For this, the backbone of pSCIL006c was amplified with the primers pSCIL_Nco_P (SEQ ID No: 24) and pSCIL_Spe_P (SEQ ID No: 25) and religated, which resulted in deletion of the kanamycin resistance cassette. The resulting plasmid was checked by sequencing and designated as pSCIL112.

2. Insertion of tetA into pSCIL112=pSCIL105

The tetracycline resistance cassette was amplified from pBR322 (D1511, Promega) with the primers tetA_5'promo_NcoI (SEQ ID No: 26) and tetA_3'_SpeI (SEQ ID No: 27). The PCR product was cleaved with the endonucleases NcoI and SpeI and cloned into the vector pSCIL112, likewise cleaved with NcoI and SpeI. Since the resulting plasmid had two copies instead of one copy of the tetracycline resistance cassette, one copy was removed by means of the Phusion Site Directed Mutagenesis Kit (F-541, Finnzymes). For this, the plasmid was amplified with the primers 105_fwd_P (SEQ ID No: 28) and 105_rev_P (SEQ ID No: 29) and religated. The resulting plasmid was checked by sequencing and designated as pSCIL105.

3. Insertion of cer into pSCIL105=pSCIL124 and pSCIL125

Figure 5:
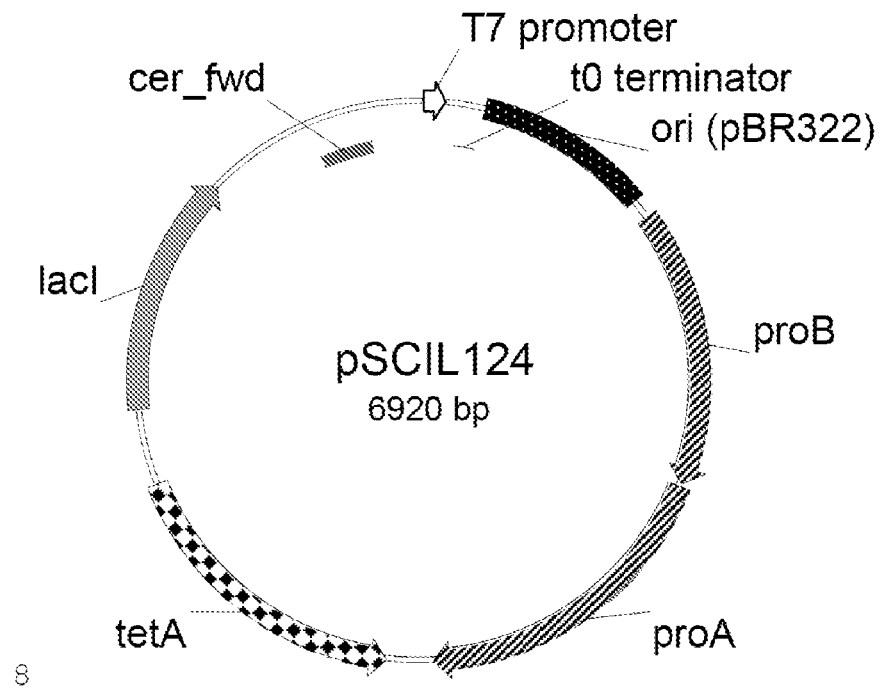
FIG. 5 schematically shows the expression vectors pSCIL124 and pSCIL125 consisting of T7 promoter, t0 terminator, pBR322-ori, proBA, tetA, lacI and cer.
Figure 5:
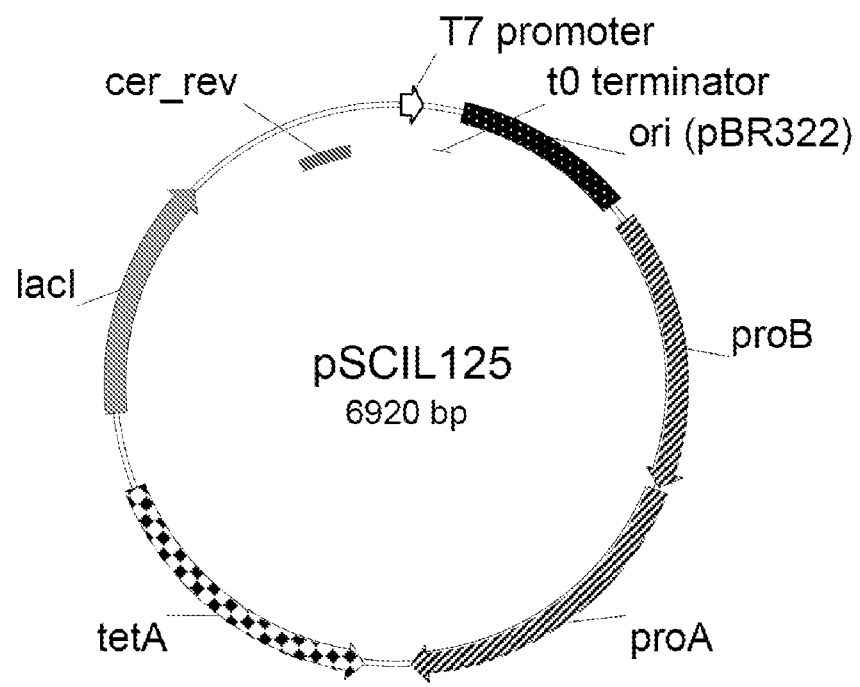

The cer element was amplified from the plasmid ColE1 (isolated from *E. coli* JC411 (DSM3877), DSMZ, by means of QIAprep Spin Miniprep, Qiagen) by PCR with the primers 5'cer_NdeI (SEQ ID NO: 21) and 3'cer_NdeI (SEQ ID NO: 22) and integrated into a unique NdeI cleavage site in pSCIL105. In this, both orientations (forward and reverse) are possible. The resulting plasmid with cer in forward orientation was designated as pSCIL124, the plasmid with cer in reverse orientation was designated as pSCIL125 and checked by sequencing (see FIG. 5, SEQ ID NO: 30).

Production of the Expression vector pSCIL129

1. Deletion of proBA in pSCIL123=pSCIL129

Figure 6:
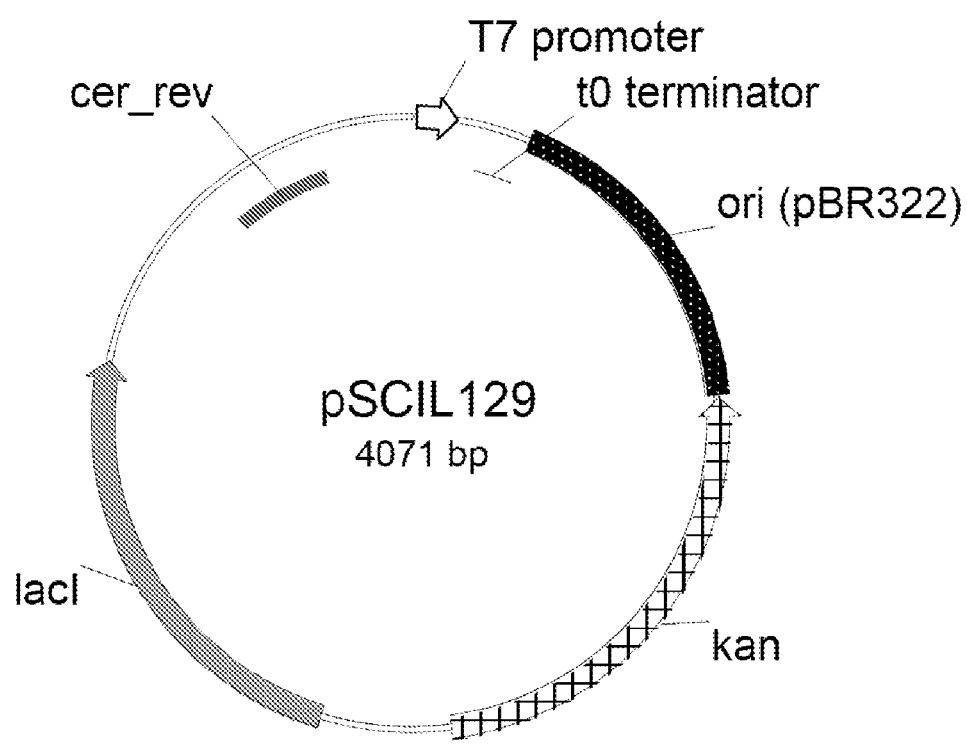
FIG. 6 schematically shows the expression vector pSCIL129 consisting of T7 promoter, t0 terminator, pBR322-ori, kan, lacI and cer.

In order to decrease the plasmid size of the expression vector, the proBA cassette was again removed. For this, the Phusion Site Directed Mutagenesis Kit (F-541, Finnzymes) was used. The plasmid pSCIL123 was amplified by means of the primers pSCIL-proBA_rev-P (SEQ ID NO: 31) and pSCIL-proBA_fwd-P (SEQ ID NO:32) such that after subsequent religation the proBA operon was deleted. The resulting expression vector was named pSCIL129 and checked by sequencing (see FIG. 6, SEQ ID NO: 33).

EXAMPLE 2

Production of an Expression System According to the Invention

The *E. coli* strains BL21 (Stratagene), HMS174 (DSM5932) and C600' (DSM426) were obtained from Stratagene or the DSMZ (Deutsche Stammsammlung für Mikroorganismen and Zellkulturen GmbH, Braunschweig). The strains BL21, HMS174 and C600' were each transformed with the plasmid pKD46 (CGSC, *E. coli* Genetic Stock Center, Yale University, New Haven, USA), which codes for the Red recombinase of the lambda phage. Thereby, targeted integration of the T7 construct into the *E. coli* genome is possible. From the resulting strains BL21 pKD46, HMS174 pKD46 and C600' pKD46, competent cells were again produced. The selection of pKD46 was effected with ampicillin on agar plates or carbenicillin in liquid cultures.

Figure 2:
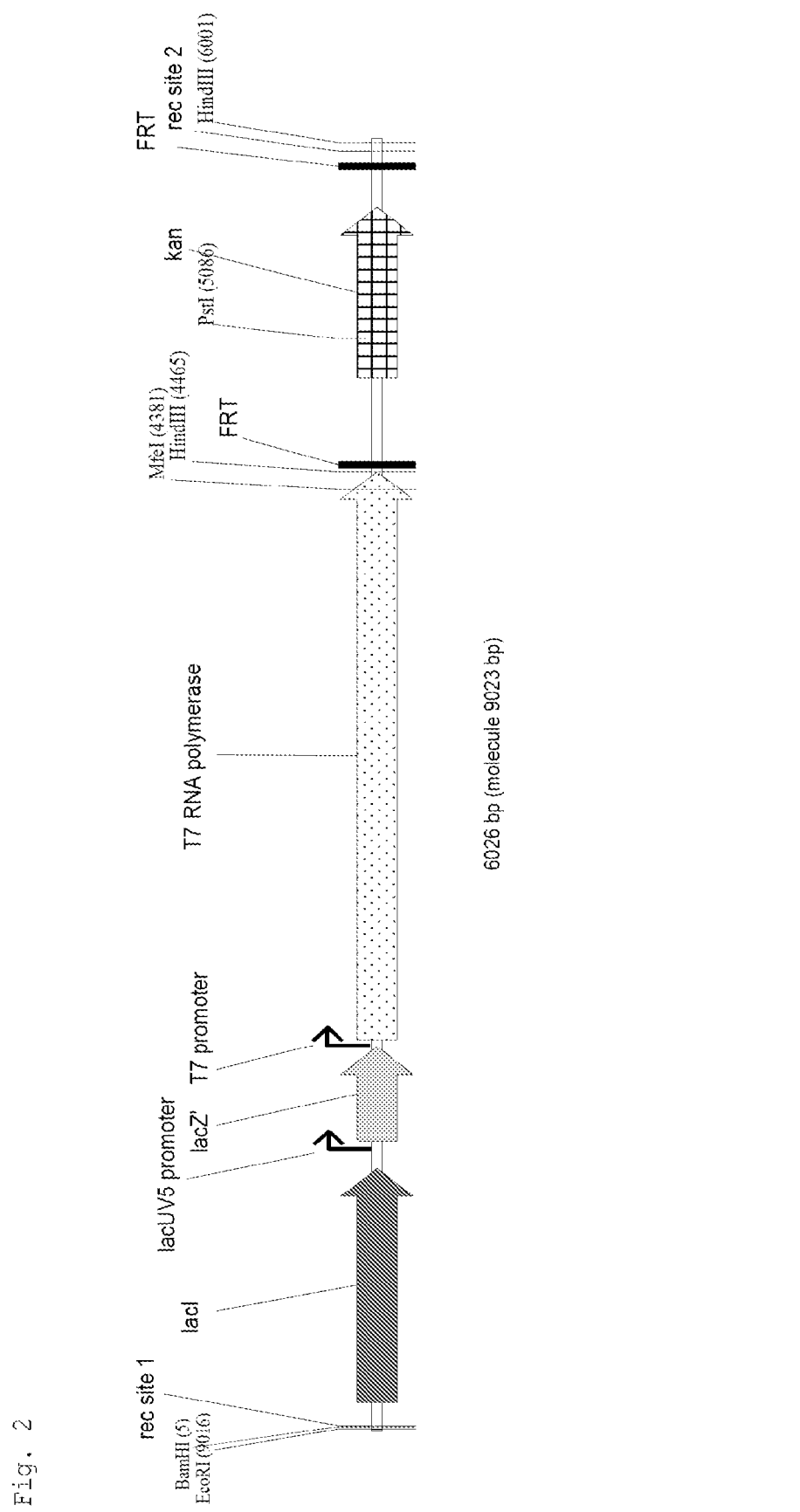
FIG. 2 schematically shows the T7 nucleotide construct consisting of lacI, lacUV5 promoter, 5' region of lacZ, T7 promoter and gene 1 of the T7 phage (T7 polymerase) and of the kanamycin resistance gene kan flanked by two FRT sites.

The DNA construct shown in FIG. 2 consisting of lacI, lacUV5 promoter, 5' region of lacZ, T7 promoter and gene 1 of the T7 phage (T7 polymerase) and the kanamycin resistance gene kan flanked by two FRT sites was produced as follows.

Firstly, the components were amplified separately and cloned together into pGEM-T easy (A1360, Promega). The gene for the T7 RNA polymerase (gene 1) was amplified with the primers T7 5'_BamHI_Xho (SEQ ID NO: 34) and T7 3'_Hind (SEQ ID NO: 35) from DNA of the T7 phage (310005, Bioron GmbH). The PCR product was purified by Qiaquick PCR Purification (Qiagen) and cloned into the vector pGEM-T easy (A1360, Promega) by means of overhanging adenine residues. The plasmid pGEM::T7 formed was checked by sequencing. The lad gene was amplified from genomic DNA of the *E. coli* strain K12 (DSM 9037, Deutschen Sammlung für Mikroorganismen und Zellkulturen GmbH; DNeasy Tissue Kit, Qiagen) by means of the primers lacI 5'_BamHI_coli (SEQ ID NO: 36) and lacI 3'_UV5_Xho (SEQ ID NO: 37). Also, the sequence of the lacUV5 promoter was integrated into the PCR product with the aid of the primer lacI 3'_UV5_Xho (SEQ ID NO:37). The PCR product was purified by Qiaquick PCR Purification (Qiagen) and cloned into the vector pGEM-T easy (A1360, Promega) by means of overhanging adenine residues. The plasmid pGEM::lacI-lacUV5 formed was checked by sequencing and then cleaved with the endonucleases BamHI and XhoI. The fragment formed was purified by QIAquick Gel Extraction Kit (Qiagen) and cloned into the likewise cleaved and purified plasmid pGEM::T7. The plasmid formed pGEM::lacI-lacUV5-T7 was checked by sequencing. The kanamycin resistance gene flanked by FRT sites was amplified with the primers Hind_pKD4 5'(SEQ ID NO: 38) and pKD4 3'_Hind_coli (SEQ ID NO: 39) from the plasmid pKD4 (CGSC, *E. coli* Genetic Stock Center, Yale University, New Haven, USA). The PCR product was cleaved with the endonuclease HindIII and cloned into the plasmid pGEM::lacI-lacUV5-T7 likewise cleaved with HindIII. The final plasmid pGEM-T easy::lacI-lacUV5-T7-kan-FRT was checked by restriction digestion with the endonucleases EcoRI and HindIII.

In order to produce a T7 nucleotide construct analogous to DE3, firstly the region consisting of lacI, lacUV5 promoter, 5' region of lacZ and the first 2574 bp of the gene 1 of the T7 phage (up to an internal MfeI cleavage site) was amplified from previously isolated genomic DNA (Genomic DNA Purification Kit, Fermentas) from BL21 (DE3) [Novagen 69387-3] by means of the primers T7_neu_BamHI_for01 (SEQ ID NO: 40) and T7 neu_MfeI_rev02 (SEQ ID NO: 41). After purification (Wizard® SV Gel and PCR, Promega), this PCR product was cleaved with the endonucleases BamHI and MfeI and after purification (Wizard® SV Gel and PCR, Promega) cloned into the 4647 bp fragment of the plasmid pGEM-T easy::lacI-lacUV5-T7-kan-FRT$^{BamHI/MfeI}$. After transformation into TOP10F' (Life Technologies) and selection on LB plates with 100 µg/ml ampicillin, the resulting plasmid pGEM-T easy::lacI-lacUV5_lacZ_T7-kan (SEQ ID NO: 42) was prepared.

Next, the whole construct was cleaved out from the plasmid pGEM-T easy::lacI-lacUV5_lacZ_T7-kan (SEQ ID NO: 42) by means of the endonuclease EcoRI. The 6026 bp fragment thus formed was purified by means of Wizard® SV Gel and PCR-Kit (Promega). The strains BL21 pKD46, HMS174 pKD46 and C600' pKD46 were then transformed with this DNA fragment and incubated overnight at room temperature in order to enable integration into the *E. coli* genome.

As a result of the choice of the flanking regions (SEQ ID NO: 43: rec site 1 and SEQ ID NO: 44: rec site 2) of the DNA construct matching the flanking regions of the proBA operon, the proBA operon is simultaneously deleted during the integration. The selection for the T7 RNA polymerase construct shown in FIG. 2 was effected by means of kanamycin in the medium. The loss of the helper plasmid pKD46 was detected through the loss of the ability to grow on ampicillin- or carbenicillin-containing media.

Figure 1:
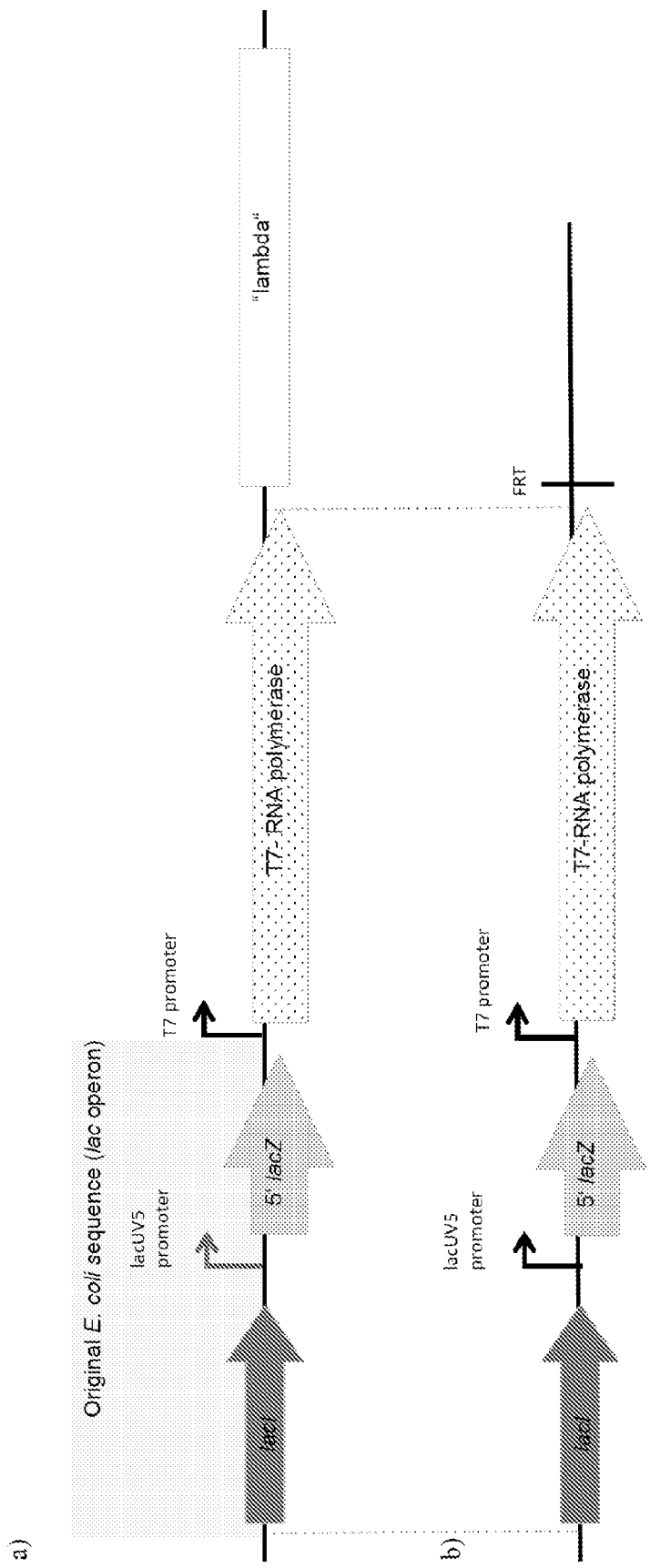
FIG. 1 schematically shows the T7 nucleotide construct in the genome of BL21 (DE3) (prior art) and BL21 ΔproBA-T7lacZ (according to the invention) in comparison;
a) DE3: integration into lambda attachment site by means of a modified lambda phage (prior art)
b) Scil-T7: targeted integration by simultaneous deletion of proBA (according to the invention)

Competent cells were produced from the resulting strains BL21 ΔproBA-T7lacZ::kan, HMS174 ΔproBA-T7lacZ::kan and C600'ΔproBA-T7lacZ::kan and transformed with the helper plasmid pCP20 (CGSC, *E. coli* Genetic Stock Center, Yale University, New Haven, USA). This step serves for the deletion of the kanamycin resistance which was also integrated into the genome in the first step, by the FLP recombinase encoded on pCP20. The selection for strains with pCP20 was effected on ampicillin-containing plates. Through incubation of the cells overnight at 43° C., the helper plasmid pCP20 is lost. The resulting strains BL21 ΔproBA-T7lacZ, HMS174 ΔproBA-T7lacZ and C600'ΔproBA-T7lacZ possess no antibiotic resistances and contain the T7 construct as shown in FIG. 1 instead of the proBA operon in the genome. The one FRT site which remains in the genome as a "scar" from the method, arises through the deletion of the kanamycin resistance cassette by the FLP recombinase. The strains were verified by Southern hybridization. In the process, the integration of the coding sequence for the T7 RNA polymerase and the deletion of proBA were detected.

The expression plasmid from Example 1 was introduced by electroporation into the strains BL21 ΔproBA-T7lacZ and HMS174 ΔproBA-T7lacZ thus obtained.

EXAMPLE 3

Comparison of the Plasmid Stability of a T7 Expression System According to the Invention and a T7 Expression System According to the Prior Art In order to study the stability of T7 expression plasmids according to the prior art and T7 expression plasmids according to the invention in BL21 (DE3) (strain from the prior art) and BL21 ΔproBA-T7lacZ (strain according to the invention), experiments were performed in shaker flasks and fed batch fermentations. For this, the gene for the human growth factor proNGF deriving from gene synthesis (Geneart, Regensburg) was cloned into the expression vectors by means of the endo-nucleases EcoRI and PstI. For the study of the plasmid stability in the shaker flask, the procedure was as follows. Firstly, precultures of the expression strains to be studied BL21 (DE3) with standard expression plasmid pSCIL006cΔproBA::proNGF (prior art), BL21 (DE3) with stable expression plasmid pSCIL129::proNGF (expression plasmid according to the invention), BL21 ΔproBA-T7lacZ with standard expression plasmid pSCIL006cΔproBA::proNGF (expression strain according to the invention with expression plasmid without plasmid stabilization system) and BL21 ΔproBA-T7lacZ with stable expression plasmid pSCIL129::proNGF (expression system according to the invention) were cultured in complex medium [34.5 g/l yeast extract (Merck 1.03753.0500), 2.475 mM $MgSO_4$, 9.347 mM $NH_4Cl$, 62 mM $K_2HPO_4$, 15 g/l glucose] with 50 µg/ml kanamycin overnight at 37° C. with shaking. On the next morning, the cells, which are necessary to inoculate a main culture to an optical density $OD_{600}$=0.2-0.3 were sterile harvested by centrifugation at 6500 rpm (5 mins). The main culture thus inoculated (20 ml complex medium without antibiotic in 100 ml Ehrlenmeyer flasks) was incubated at 37° C. with shaking at 210 rpm until an $OD_{600}$=0.8 was reached. At this time, the target gene expression was induced by addition of 1 mM IPTG. Three hours (3 h pi (post induction)) and 24 h after addition of the inducer (24 h pi), sterile dilutions of the cultures were produced and plated out onto LB medium [5 g/l yeast extract (Merck 1.03753.0500), 10 g/l soya peptone (Merck 1.07212.0500), 85.56 mM NaCl]. These plates were incubated overnight at 37° C. From the grown colonies in each case 100 colonies were pricked out in parallel onto LB and LB+50 µg/ml kanamycin. A plasmid stability of for example 10% thus means that only 10% of the colonies grown on LB also grew on LB+kanamycin. The colonies which can grow on LB+kanamycin still possess the expression plasmids. Colonies which can only grow on LB have lost the expression plasmids. In each case, four independent experiments were performed in order to draw conclusions on the plasmid stabilities. The results are shown in Tab. 1 as mean values with standard deviations.

TAB. 1

Plasmid stability of a standard expression plasmid according to the prior art (pSCIL006cΔproBA::proNGF) and an expression plasmid according to the invention (pSCIL129::proNGF) in BL21 (DE3) (strain according to the prior art) and BL21 ΔproBA-T7lacZ (strain according to the invention) in shaker flask

| | BL21 (DE3) | | BL21 ΔproBA-T7lacZ | |
|---|---|---|---|---|
| Time | pSCIL006cΔproBA::proNGF | pSCIL129::proNGF | pSCIL006cΔproBA::proNGF | pSCIL129::proNGF |
| 3 h pi | 86% ± 4 | 100% | 90% ± 7 | 100% |
| 24 h pi | 5% ± 6 | 88% ± 6 | 84% ± 18 | 99% ± 1 |

It was found that the expression system according to the prior art displays very low plasmid stabilities of 86% 3 h after induction and only 5% 24 h after induction. Through the stabilization of the expression plasmid by means of cer according to the invention an increase in the plasmid stability to 100% 3 h after induction and 88% 24 h after induction is possible in BL21 (DE3). An increase in the plasmid stability to ca. 100% 24 h after induction could only be achieved through the use of a T7 expression system according to the invention, consisting of BL21 ΔproBA-T7lacZ with stable expression plasmid pSCIL129::proNGF. Surprisingly however, a standard expression plasmid in BL21 ΔproBA-T7lacZ also showed a high plasmid stability of 90% 3 h after induction and 84% 24 h after induction, whereas at the same time the same plasmid in BL21 (DE3) had already been essentially lost (5% 24 h pi). As the target gene in these experiments, the human growth factor proNGF was expressed. The expression of proNGF was checked by SDS-PAGE.

Apart from this, the expression system according to the invention was compared with the prior art in fed batch fermentations. Firstly, precultures of the expression strains to be studied BL21 (DE3) with standard expression plasmid pSCIL006cΔproBA::proNGF (prior art), BL21 (DE3) with stable expression plasmid pSCIL129::proNGF (expression plasmid according to the invention), BL21 ΔproBA-T7lacZ with standard expression plasmid pSCIL006cΔproBA::proNGF (expression strain according to the invention with expression plasmid without plasmid stabilization system) and BL21 ΔproBA-T7lacZ with stable expression plasmid pSCIL129::proNGF (expression system according to the invention) were cultured in complex medium [34.5 g/l yeast extract (Merck 1.03753.0500), 2.475 mM $MgSO_4$, 9.347 mM $NH_4Cl$, 62 mM $K_2HPO_4$, 15 g/l glucose] with 50 µg/ml kanamycin overnight at 37° C. with shaking. For the fermentation, in each case 2 l complex medium without antibiotic [50 g/l yeast extract (Biospringer 0206), 2.475 mM $MgSO_4$, 9.347 mM $NH_4Cl$, 62 mM $K_2HPO_4$, 10 g/l glucose, 0.2 ml/l antifoam Synperonic (Croda ETK0879)] are placed in 5 l laboratory fermenters and inoculated with precultures of the expression strains such that a starting $OD_{600}$ (optical density at 600 nm) of 0.06 was reached. After 6.5 h, after the glucose had been consumed, the fed batch phase was started by addition of substrate. The substrate feed flow here takes place according to an exponential function of the form feedflow=const*exp($\mu_1$*t). Wherein $\mu$ is the specific growth rate for which $\mu_1$=const<$\mu_{max}$ applies, i.e. the glucose concentration instantaneously available always lies below the maximal instantaneous demand of the microorganisms, as a result of which a submaximal growth rate is achieved and accumulation of glucose is prevented. For example, a value $\mu_1$ =0.25 $h^{-1}$ is set. At a defined optical density, e.g. $OD_{600}$=50±5, the protein expression is induced by addition of IPTG, e.g. 1 mM. At this time, the substrate feed flow is reduced by 70% linearly over 6 h and then kept constant. The process ends after a defined induction period, e.g. 24 h.

On attainment of an $OD_{600}$=50±5, the target gene expression was induced by addition of 1 mM IPTG. At this time and 6 h, 8 h and 24 h after induction, the plasmid stabilities were analyzed as described above and the expression of the human growth factor proNGF checked. The data are shown in Tab. 2.

TAB. 2

Plasmid stability of a standard expression plasmid (pSCIL006cΔproBA::proNGF) and an expression plasmid according to the invention (pSCIL129::proNGF) in BL21 (DE3) and BL21 ΔproBA-T7lacZ in fed batch fermentations

| | | BL21 (DE3) | | BL21 ΔproBA-T7lacZ | |
|---|---|---|---|---|---|
| Time | | pSCIL006cΔproBA::proNGF | pSCIL129::proNGF | pSCIL006cΔproBA::proNGF | pSCIL129::proNGF |
| Induction | $OD_{600}$ | 51.6 | 52.2 | 46.1 | 47.2 |
| | PS | 100% | 100% | 100% | 100% |
| 6 h pi | $OD_{600}$ | 97.4 | 101.2 | 99.0 | 106.9 |
| | PS | 11% | 100% | 94% | 100% |

TAB. 2-continued

Plasmid stability of a standard expression plasmid (pSCIL006cΔproBA::proNGF) and an expression plasmid according to the invention (pSCIL129::proNGF) in BL21 (DE3) and BL21 ΔproBA-T7lacZ in fed batch fermentations

| | | BL21 (DE3) | | BL21 ΔproBA-T7lacZ | |
|---|---|---|---|---|---|
| Time | | pSCIL006c ΔproBA:: proNGF | pSCIL129:: proNGF | pSCIL006c ΔproBA:: proNGF | pSCIL129:: proNGF |
| 8 h pi | OD$_{600}$ PS | 97.4 13% | 103.6 100% | 101.6 89% | 108.9 100% |
| 24 h pi | OD$_{600}$ PS | 106.6 2% | 98.8 100% | 113.6 95% | 122.9 100% |

(PS: plasmid stability)

It was found that in a fed batch fermentation the expression system according to the prior art has already lost 89% of the expression plasmids 6 h after induction (PS 11%), whereas the expression system according to the invention displays a plasmid stability of 100% even 24 h after induction. Here both the expression plasmid according to the invention with plasmid stabilization system cer (pSCIL129::proNGF) and also the expression strain according to the invention BL21 ΔproBA-T7lacZ have clear advantages over the expression system according to the prior art, since here the plasmid stabilities 24 h after induction, at 100% and 95% respectively, lie significantly higher than in the expression system according to the prior art, at 2%.

In order to study further the stability of T7 expression plasmids according to the invention in BL21 (DE3) and BL21 ΔproBA-T7lacZ, further experiments in shaker flasks were performed. For this, the gene for human prethrombin deriving from gene synthesis (Geneart, Regensburg) was cloned into the expression vectors pSCIL006c (usual expression plasmid) and pSCIL123 (stable expression plasmid) by means of the endonucleases EcoRI and PstI. For the study of the plasmid stability in the shaker flask, the procedure as described above was used. Results are shown in Tab. 3.

TAB. 3

Plasmid stability of a standard expression plasmid (pSCIL006c::preThrombin) and an expression plasmid according to the invention (pSCIL123::preThrombin) in BL21 (DE3) and BL21 ΔproBA-T7lacZ

| | BL21 (DE3) | | BL21 ΔproBA-T7lacZ | |
|---|---|---|---|---|
| Time | pSCIL006c:: preThrombin | pSCIL123:: preThrombin | pSCIL006c:: preThrombin | pSCIL123:: preThrombin |
| 3 h pi | 5% ± 5 | 100% | 6% ± 3 | 100% |
| 24 h pi | 1% ± 0 | 41% ± 1 | 1% ± 2 | 78% ± 5 |

It was found that the expression system according to the prior art displayed extremely low plasmid stabilities. Already 3 h after induction, only 5% plasmid-bearing strains were still present and after 24 h almost all cells were plasmid-free. Through the use of the expression plasmid pSCIL123::preThrombin a plasmid stability of 100% 3 h after induction could be achieved in both expression strains BL21 (DE3) and BL21 ΔproBA-T7lacZ. At time 24 h after induction, the plasmid stability of the expression system according to the invention (BL21 ΔproBA-T7lacZ with pSCIL123::preThrombin), at 78%, is approximately twice as high as in the expression strain according to the prior art (BL21 (DE3) pSCIL123::preThrombin), at 41%. Expression of the human preThrombin was checked by SDS-PAGE.

The invention claimed is:

1. An expression system comprising a prokaryotic cell containing a nucleotide construct coding for a T7 RNA polymerase under control of a T7 promoter and under control of an inducible promoter, and an expression vector, which contains a gene encoding a protein to be expressed under control of the T7 promoter, wherein: (a) the prokaryotic cell contains no lambda phage DNA, (b) the prokaryotic cell is a cell of an Escherichia coli strain with the T7 RNA polymerase gene in a genome thereof, and (c) the expression vector contains a plasmid stabilization system.

2. The expression system as claimed in claim 1, wherein the plasmid stabilization system is a member selected from the group consisting of multimer resolution systems (mrs), partitioning systems (par) and postsegregational killing systems (PSK).

3. An expression system comprising a prokaryotic cell containing a nucleotide construct coding for a T7 RNA polymerase under control of a T7 Promoter and under control of an inducible promoter, and an expression vector, which contains a gene encoding a protein to be expressed under control of the T7 promoter, wherein: (a) the prokaryotic cell contains no lambda phage DNA, (b) the expression vector contains a plasmid stabilization system and (c) the nucleotide construct comprises SEQ ID NO: 1.

4. A method for producing a recombinant protein, said method comprising:
providing an expression system as claimed in claim 1,
fermenting the expression system under antibiotic-free conditions which are suitable for expression of the T7 RNA polymerase and expression of the recombinant protein,
expressing the recombinant protein, and
isolating the recombinant protein.

5. The method as claimed in claim 4, wherein a targeted integration of the T7 RNA polymerase under control of the inducible promoter is effected into a proBA sequence of E. coli.

6. The expression system as claimed in claim 3, wherein a targeted integration of the T7 RNA polymerase under control of the inducible promoter is effected into a proBA sequence of E. coli.

7. A method for producing a recombinant protein, said method comprising:
   providing an expression system as claimed in claim 3,
   fermenting the expression system under antibiotic-free conditions which are suitable for expression of the T7 RNA polymerase and expression of the recombinant protein,
   expressing the recombinant protein, and
   isolating the recombinant protein.

* * * * *